United States Patent
Desalles et al.

(10) Patent No.: US 10,035,013 B2
(45) Date of Patent: Jul. 31, 2018

(54) SUBCUTANEOUS ELECTRODES FOR CRANIAL NERVE STIMULATION

(71) Applicants: THE REGENTS OF THE UNIVERSITY OF CALIFORNIA, Oakland, CA (US); NEUROSIGMA, INC., Los Angeles, CA (US)

(72) Inventors: Antonio A. F. Desalles, Los Angeles, CA (US); Alessandra Gorgulho, Los Angeles, CA (US); Christopher M. DeGiorgio, Valencia, CA (US); Ian A. Cook, Los Angeles, CA (US); Colin Kealey, Los Angeles, CA (US); Leon Ekchian, Glendale, CA (US); Patrick Miller, Santa Monica, CA (US)

(73) Assignees: THE REGENTS OF THE UNIVERSITY OF CALIFORNIA, Oakland, CA (US); NEUROSIGMA, INC., Los Angeles, CA (US)

(*) Notice: Subject to any disclaimer, the term of this patent is extended or adjusted under 35 U.S.C. 154(b) by 68 days.

(21) Appl. No.: 14/390,986

(22) PCT Filed: Apr. 5, 2013

(86) PCT No.: PCT/US2013/035499
§ 371 (c)(1),
(2) Date: Oct. 6, 2014

(87) PCT Pub. No.: WO2013/152316
PCT Pub. Date: Oct. 10, 2013

(65) Prior Publication Data
US 2015/0119898 A1 Apr. 30, 2015

Related U.S. Application Data
(60) Provisional application No. 61/620,879, filed on Apr. 5, 2012.

(51) Int. Cl.
*A61N 1/36* (2006.01)
*A61N 1/05* (2006.01)
*A61B 17/34* (2006.01)

(52) U.S. Cl.
CPC ........ *A61N 1/0558* (2013.01); *A61B 17/3421* (2013.01); *A61N 1/0504* (2013.01);
(Continued)

(58) Field of Classification Search
CPC .. A61N 1/0504; A61N 1/0526; A61N 1/0551; A61N 1/0553; A61N 1/0558;
(Continued)

(56) References Cited

U.S. PATENT DOCUMENTS 7,769,461 B2 * 8/2010 Whitehurst ....... A61M 5/14276
607/45
8,214,057 B2 * 7/2012 Barolat .............. A61B 5/04001
607/117

(Continued)

FOREIGN PATENT DOCUMENTS

EP 2 092 951 A1 8/2009
WO 2007/041604 A2 4/2007
(Continued)

OTHER PUBLICATIONS

Johnson et al. "Peripheral Stimulation for Treatment of Trigeminal Postherpetic Neuralgia and Trigeminal Posttraumatic Neuropathic Pain: A Pilot Study." Neurosurgery. Jul. 2004;55(1):135-41; discussion 141-2.*

(Continued)

*Primary Examiner* — Eugene T Wu
(74) *Attorney, Agent, or Firm* — Vista IP Law Group LLP

(57) ABSTRACT

An implantable subcutaneous electrode system is disclosed. The implantable subcutaneous electrode system may include an electrode body with electrical contacts disposed thereon
(Continued)

or integrally formed therein. The electrode body also may include an insulation region defined between the electrical contacts and an aperture defined in the electrode body for receiving an anchoring device. A minimally invasive delivery device and methods for delivery of an implantable electrode system is also provided. The methods may include steps of introducing a needle comprising a cannula and a stylet through a patient's skin, removing the stylet while leaving the cannula in place, introducing an electrode applicator through the cannula, the electrode applicator comprising a hollow driver which receives the electrode assembly, and anchoring the electrode assembly to a bone by driving the hollow driver such that a self-tapping screw within the electrode assembly screws into the bone.

4 Claims, 25 Drawing Sheets

(52) U.S. Cl.
CPC .......... *A61N 1/0526* (2013.01); *A61N 1/0553* (2013.01); *A61N 1/36182* (2013.01); *A61N 1/36064* (2013.01)

(58) Field of Classification Search
CPC ........... A61N 2011/36039; A61N 2011/36057; A61N 2011/3605–2011/36125
See application file for complete search history.

(56) References Cited

U.S. PATENT DOCUMENTS

| | | | | |
|---|---|---|---|---|
| 8,428,734 B2* | 4/2013 | Rigaux | ................ | A61N 1/0456 607/139 |
| 8,958,880 B2* | 2/2015 | DeGiorgio | ........... | A61N 1/0456 607/45 |
| 9,511,223 B2* | 12/2016 | DeGiorgio | ........... | A61N 1/0456 |
| 2002/0103521 A1 | 8/2002 | Swoyer et al. | | |
| 2007/0150034 A1* | 6/2007 | Rooney | ................ | A61N 1/0531 607/115 |
| 2008/0140152 A1* | 6/2008 | Imran | ................... | A61N 1/0553 607/46 |
| 2008/0188917 A1 | 8/2008 | Gerber et al. | | |
| 2010/0070010 A1* | 3/2010 | Simpson | .............. | A61N 1/0553 607/117 |
| 2010/0274313 A1* | 10/2010 | Boling | ................. | A61N 1/0546 607/46 |
| 2011/0093033 A1* | 4/2011 | Nekhendzy | ........ | A61N 1/36017 607/46 |
| 2011/0106220 A1 | 5/2011 | DeGiorgio et al. | | |
| 2011/0112603 A1 | 5/2011 | DeGiorgio et al. | | |
| 2012/0203301 A1* | 8/2012 | Cameron | ............... | A61N 1/361 607/45 |
| 2012/0271189 A1* | 10/2012 | Nelson | ................. | A61B 5/0476 600/544 |
| 2014/0142669 A1* | 5/2014 | Cook | ................... | A61N 1/0551 607/116 |
| 2014/0206945 A1* | 7/2014 | Liao | ..................... | A61N 1/0529 600/301 |

FOREIGN PATENT DOCUMENTS

| WO | 2012/082961 A2 | 6/2012 |
|---|---|---|
| WO | 2012/082961 A3 | 6/2012 |

OTHER PUBLICATIONS

Neurosigma: Journal Articles. <http://www.neurosigma.com/journal-articles.html>. Accessed Dec. 19, 2016.*
The extended European search report dated Nov. 5, 2015 in European Patent Application No. 13772822.6-1652, Applicant: The Regents of the University of California, et al., (8pages).
Communication pursuant to Rules 70(2) and 70a(2) EPC dated Nov. 24, 2015 in European Patent Application No. 13772822.6-1652, Applicant: The Regents of the University of California, et al., (1page).
Patent Examination Report No. 1 dated Oct. 24, 2016 in Australian Patent Application No. 2013243309, Applicant: The Regents of the University of California et al., (3pages).
Notice of Reasons for Rejection dated Dec. 9, 2016 in Japanese Patent Application No. 2015-504752, (11pages).
Patent Examination Report No. 2 dated Jan. 9, 2017 in Australian Patent Application No. 2013243309, (3pages).
Communication under Rule 71(3) EPC dated Apr. 20, 2017 in European Application No. 13 772 822.6-1666, Applicant: The Regents of the University of California, (8pages).
Notice of Reasons for Rejection dated Aug. 23, 2017 in Japanese Application No. 2015-504752, Applicant: The Regents of the University of California, (7pages).

* cited by examiner

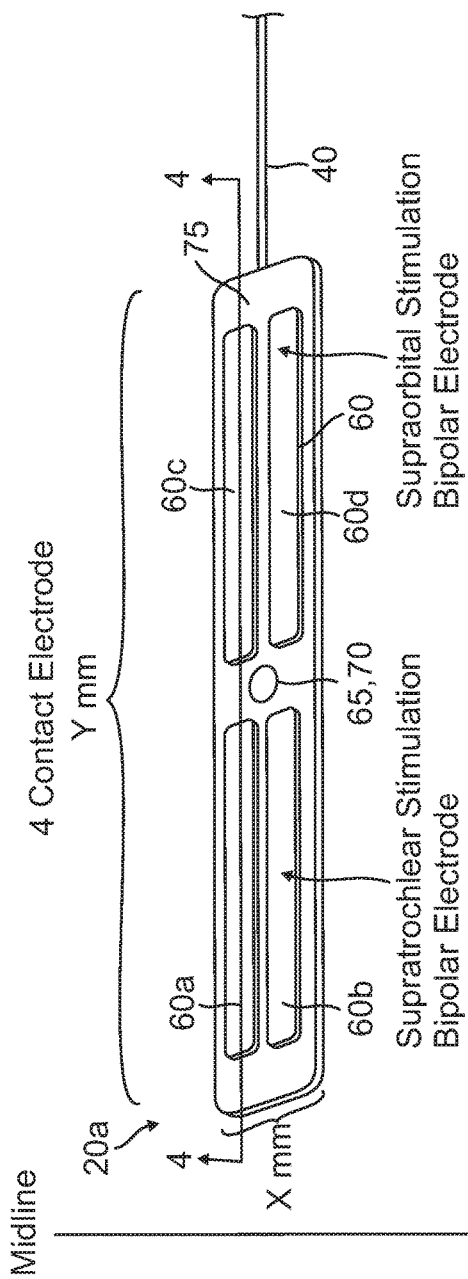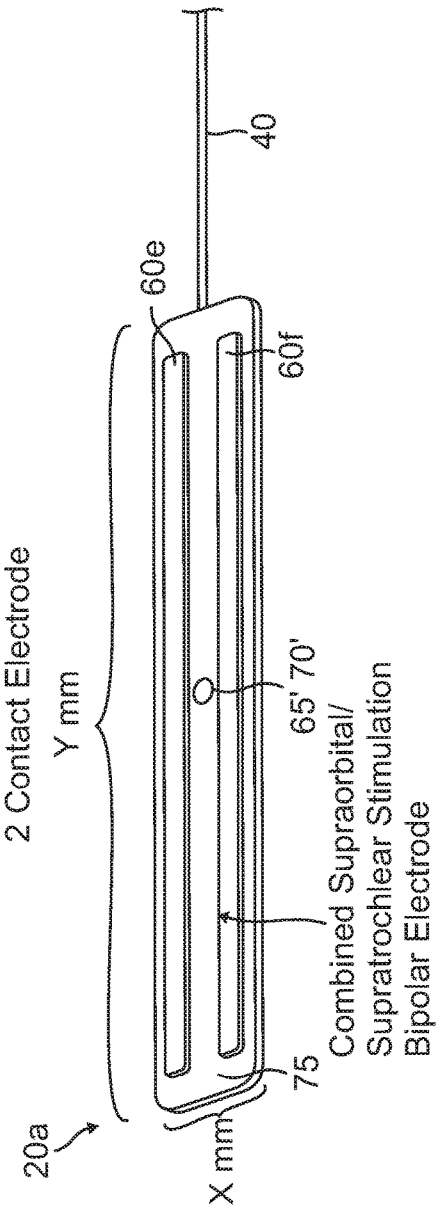
FIG. 3A-1
FIG. 3A-2

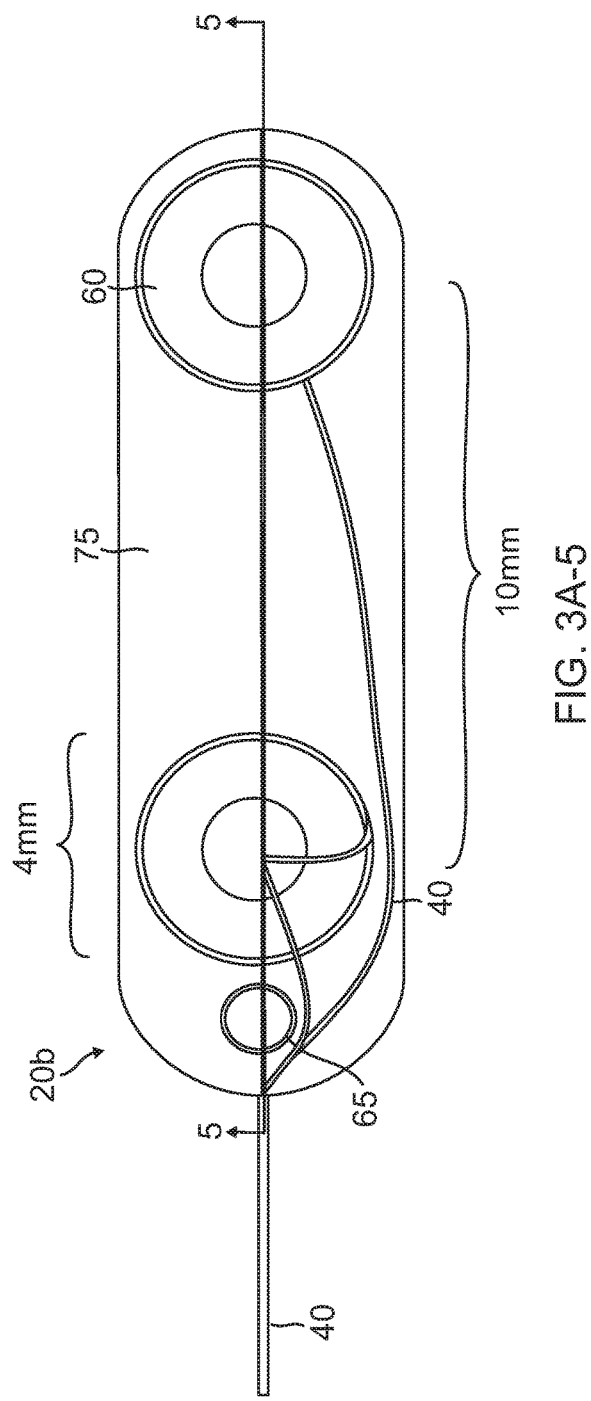
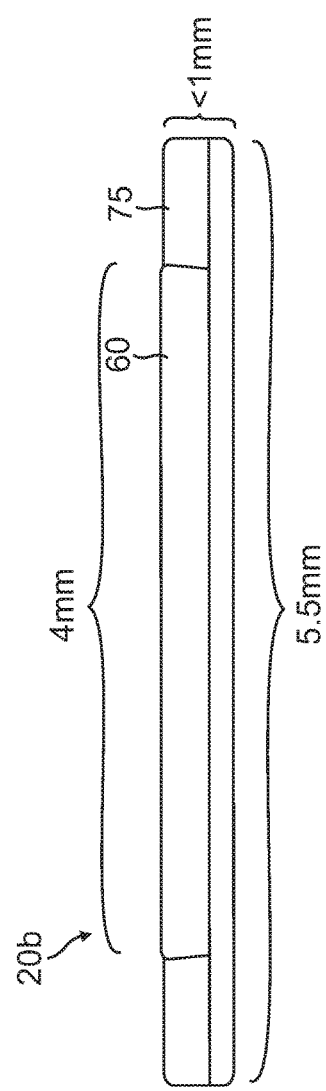

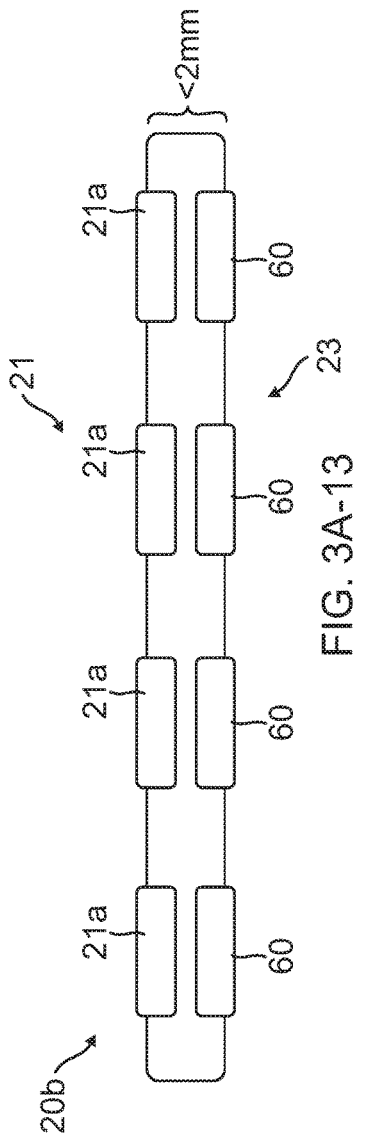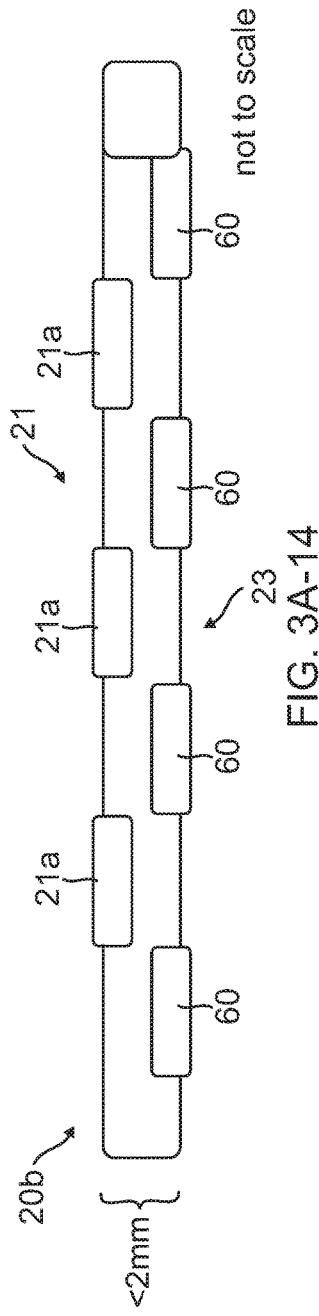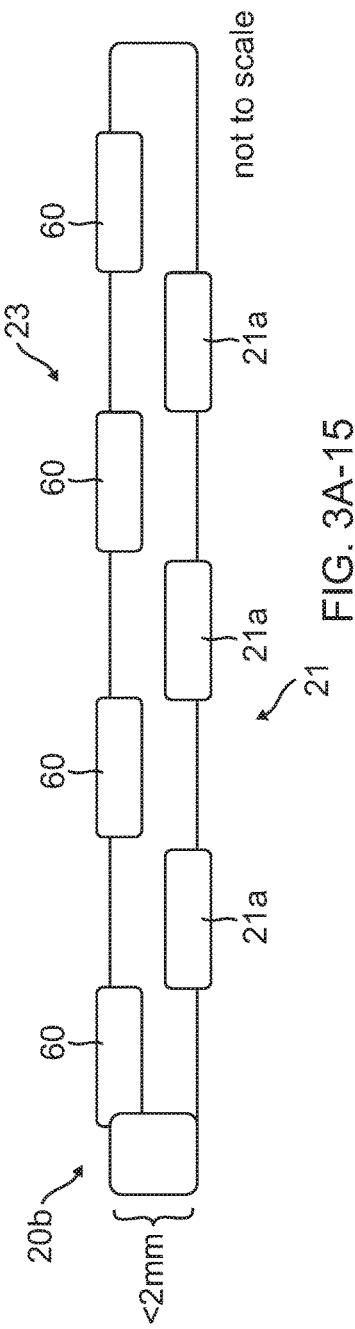

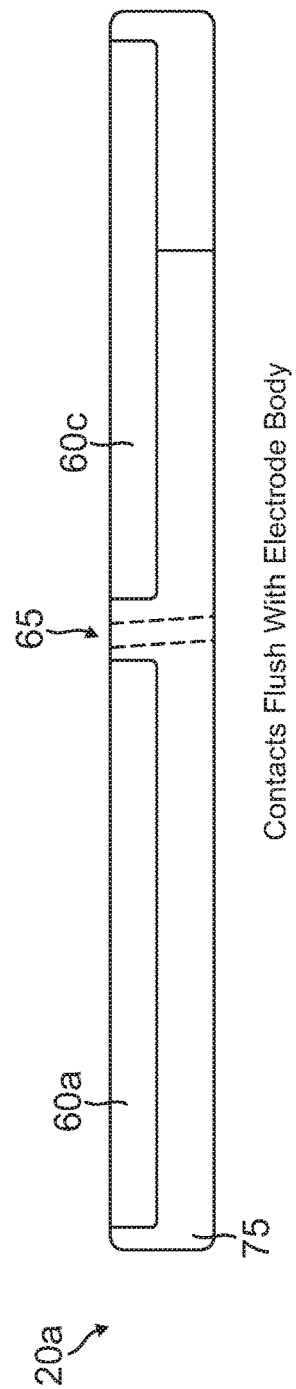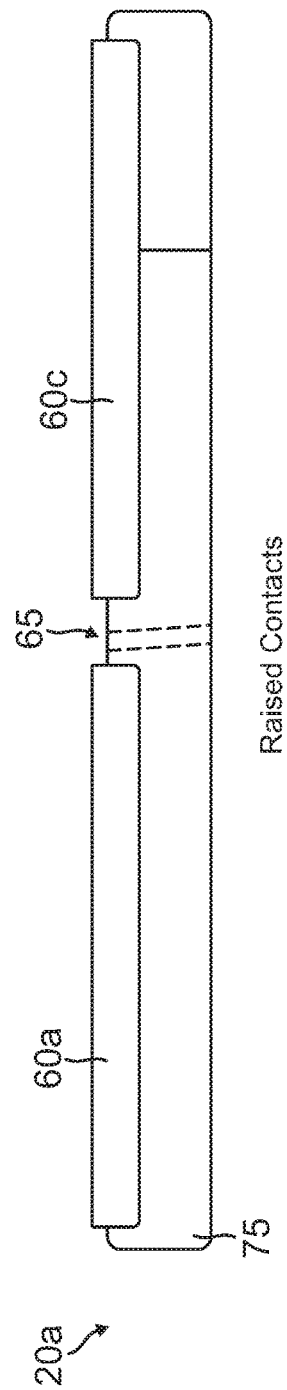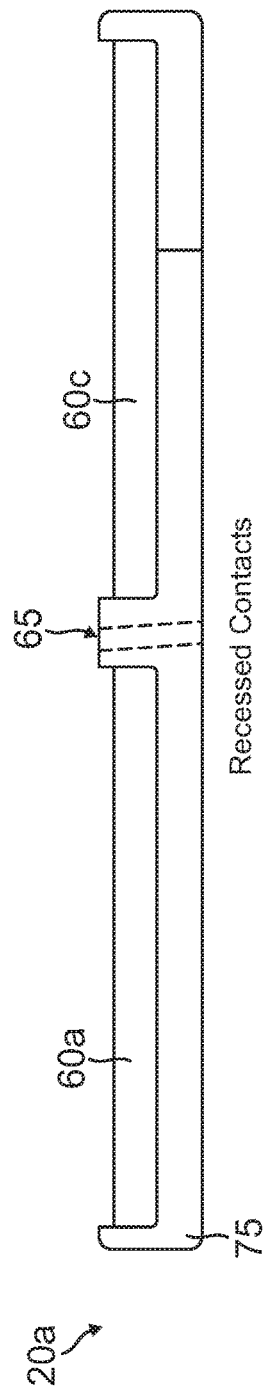

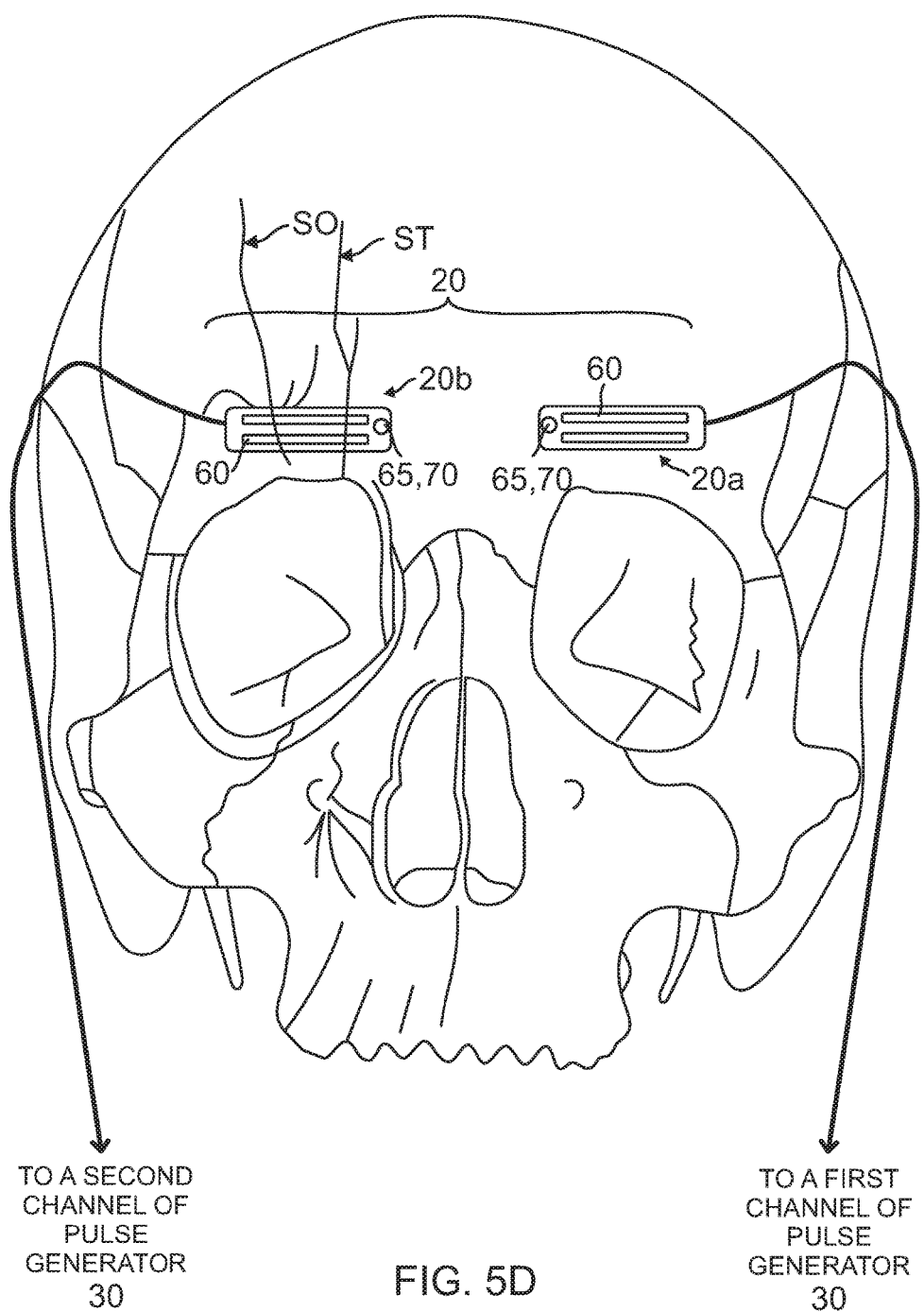

SUBCUTANEOUS ELECTRODES FOR CRANIAL NERVE STIMULATION

CROSS-REFERENCE TO RELATED APPLICATION

This Application is a U.S. National Stage filing under 35 U.S.C. § 371 of PCT Patent Application No. PCT/US2013/035499, filed Apr. 5, 2013, which claims priority to U.S. Provisional Patent Application No. 61/620,879 filed on Apr. 5, 2012. The contents of the aforementioned applications are incorporated by reference herein. Priority is expressly claimed in accordance with 35 U.S.C. §§ 119, 120, 365 and 371 and any other applicable statutes.

GOVERNMENT RIGHTS

This work was supported by the U.S. Department of Veterans Affairs, and the Federal Government has certain rights in the invention.

TECHNICAL FIELD

The present disclosure relates to implantable neurostimulation systems. More specifically the present disclosure relates to implantable electrode systems and methods for implanting and fixing the same for stimulation of cranial nerves.

BACKGROUND

For some medical disorders, brain stimulation has been a primary treatment alternative to pharmacotherapy, and electroconvulsive therapy (ECT, or "electroshock" therapy) has been the dominant brain stimulation approach since the first part of the 20th century. ECT carries risks of memory and other cognitive side effects, considerable cost, and risks of anesthesia. Two implantable approaches have also been described: deep brain stimulation (DBS), in which electrodes are implanted directly within the brain, and vagus nerve stimulation (VNS) in which stimulating electrodes are implanted on the vagus nerve in the neck. While the U.S. Food and Drug Administration (FDA) have approved systems for deep brain stimulation for the treatment of Parkinson's disease, DBS is presently an experimental intervention for other neuropsychiatric conditions. The risks of DBS include infection, hemorrhage, and injury to deep brain structures. In reports of clinical studies with VNS, many of the patients who undergo VNS treatments do not achieve remission, and there is no reliable predictor of good outcomes from the implanted VNS device.

A far safer and less invasive implantation approach has been developed by for the stimulation of the trigeminal nerves. For example, the ophthalmic nerves ascend from foramen above the eyes and ascend toward the hairline. These nerves are relatively superficial in that the plate-like portion of the skull (the squama frontalis) that defines the forehead is itself quite superficial with regard to the forehead skin surface. There is thus a relatively thin portion of subcutaneous tissue, fascia, and muscle between the forehead skin surface and the underlying bone.

In its least invasive form, a cutaneous electrode is applied to the forehead to stimulate the ophthalmic nerves. Such an application is quite advantageous in that a lay person can readily center an appropriate "bandaid" electrode on their forehead adjacent or above their eyebrows. Thus, a lay person can readily position the cutaneous electrode without requiring any specialized knowledge or training. Moreover, the superficial depth of the ophthalmic nerves on the forehead means that the nerves are readily stimulated by current levels that are easily tolerated by patients. The amount of current may thus be regulated so that the brain itself is never subjected to any current (or subjected to such vanishingly small amounts of current that the currents have no deleterious effects). In contrast, it was conventional to propose the implantation of electrodes on the trigeminal nucleus. This invasive implantation is fraught with dangers of meningitis and nerve damage. But even if it were done safely, the resulting excitation is so close to the brain that the brain is then exposed to harmful amounts of current. In contrast, a cutaneous electrode application to the forehead involves none of the risks involved with the conventional invasive approaches and also isolates the brain from exposure to electrical current. What is even more remarkable is that the cutaneous stimulation of the ophthalmic has proven to be more clinically efficacious than conventional invasive approaches such as implantation on the vagus nerve for treatment of disorders such as epilepsy.

The cutaneous electrodes typically need only be applied at night before a patient sleeps. The electrodes can then be removed upon waking so that a patient can resume a normal routine during the daytime hours. Although a cutaneous stimulation of the ophthalmic nerves is thus not only safer but more efficacious than conventional treatments, the electrodes must be worn during the therapy—they cannot stimulate the ophthalmic nerves at a distance. There may be certain patients who cannot tolerate the nightly application of the electrodes. Moreover, it may be the case that the neurostimulation therapy needs to be applied throughout the day as well. A patient would naturally be reluctant to be out in the public even with flesh-colored electrodes on their forehead. For such patients, subcutaneous neurostimulation therapies are indicated. In that regard, a subcutaneous electrode by definition may be placed closer to a targeted nerve or in actual contact with a targeted nerve as opposed to an overlying cutaneous electrode. So a subcutaneous approach has the advantage of a more direct stimulation of the targeted nerve and enables the use of less current as well.

Accordingly, there is a need in the art for cutaneous electrodes for neurostimulation of nerves such as the ophthalmic nerves and corresponding implantation techniques.

SUMMARY

To address the aforementioned needs, various techniques and devices are disclosed. For example, an electrode assembly including a self-tapping screw having an electrically active hexagonally shaped head region is disclosed. The screw includes a bone engaging surface and a wire engaging surface; an electrode wire having a distal end electrically coupled to the wire engaging surface of the screw and a proximal end configured to electrically couple to a pulse generator.

A method of percutaneously implanting an electrode assembly including a self-tapping screw in a patient is also disclosed herein. The method includes the steps of introducing a needle comprising a cannula and a stylet through the patient's skin; removing the stylet while leaving the cannula in place; introducing an electrode applicator through the cannula, the electrode applicator comprising a hollow driver which receives the electrode assembly; and anchoring the electrode assembly to a bone by driving the hollow driver to such that a self-tapping screw within the electrode assembly screws into the bone. For example, the method may comprise the steps of: inserting the stylet through the skin towards a nerve to introduce the cannula adjacent the nerve; inserting a hollow driver through the cannula, the hollow driver having a lumen including the electrode assembly, wherein the electrode assembly includes a self-tapping screw and a lead electrically coupled to the self-tapping screw; and using the hollow driver to drive the self-tapping screw into bone adjacent the nerve to attach the electrode assembly to the bone.

An implantable electrode assembly is disclosed herein. In one aspect, the assembly includes an electrode body having a medial end and a lateral end; at least two electrical contacts disposed on or integrally formed in the electrode body; an insulating region defined between the at least two electrical contacts; and at least one aperture defined in the electrode body, wherein the aperture is configured to receive an anchoring device. For example, the implantable electrode assembly may include: an electrode body having a distal side, a proximal side, a medial end, and a distal end; a pair of electrical contacts disposed on or integrally formed in the electrode body such that one of the electrical contacts in the pair is located distally towards the distal side and a remaining one of the electrical contacts in the pair is located proximally towards the proximal side, wherein each electrical contact extends between the medial end and the distal end such that the first pair of electrical contacts is configured to excite a fiber-directed current along a supraorbital nerve and along an adjacent supratrochlear nerve; an insulating region defined between the electrical contacts; and an aperture defined in the electrode body, wherein the aperture is configured to receive an anchoring device.

In another embodiment, an electrode assembly is provided that includes: an electrode body having a distal side and a proximal side; a first pair of electrical contacts disposed on or integrally formed in the electrode body such that one of the electrical contacts in the first pair is located distally towards the distal side and a remaining one of the electrical contacts in the first pair is located proximally towards the proximal side; a second pair of electrical contacts disposed on or integrally formed in the electrode body such that one of the electrical contacts in the second pair is located distally towards the distal side and a remaining one of the electrical contacts in the second pair is located proximally towards the proximal side, wherein the second pair of electrical contacts is spaced apart from the first pair of electrical contacts such that the first pair of electrical contacts is configured to excite a fiber-directed current along a supraorbital nerve and such that the second pair of electrical contacts is configured to excite a fiber-directed current along an adjacent supratrochlear nerve; an insulating region defined between the pairs of electrical contacts and between each electrical contact in each pair; and an aperture defined in the electrode body, wherein the aperture is configured to receive an anchoring device.

In another embodiment, an electrode assembly is provided that includes: an electrode body having a medial end and an opposing distal end; a pair of electrical contacts disposed on or integrally formed in the electrode body such that one of the electrical contacts in the pair is located medially towards the medial end and a remaining one of the electrical contacts in the pair is located laterally towards the lateral end, the pair of electrical contacts being spaced apart such that the pair of electrical contacts are configured to excite an orthogonally-directed current across a supraorbital nerve and across an adjacent supratrochlear nerve; an insulating region defined between the electrical contacts; and an aperture defined in the electrode body, wherein the aperture is configured to receive an anchoring device.

In yet another alternative embodiment, a method of implanting a cutaneous electrode is provided that includes the acts of: forming an incision through the skin adjacent a supraorbital foramen such that the incision extends through an adjacent frontalis muscle to underlying loose connective tissue; within the incision, displacing a portion of the frontalis muscle away from the underlying loose connective tissue such that an associated supraorbital nerve and an associated supratrochlear nerve displace with the displaced portion of the frontalis muscle; positioning a cutaneous electrode into the loose connective tissue adjacent the displaced portion of the frontalis muscle such that the cutaneous electrode is positioned to excite the associated supraorbital nerve and the associated supratrochlear nerve; and inserting an anchoring device through an aperture in the cutaneous electrode and anchoring the anchoring device to bone underlying the loose connective tissue.

This summary is provided to introduce a selection of concepts in a simplified form that are further described below. This summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

The present disclosure, both as to its organization and manner of operation, may be understood by reference to the following description, taken in connection with the accompanying drawings, in which:

FIGS. 3A-1 and 3A-2 depict various embodiments of an electrode assembly that may be used in the system of FIG. 2;

FIG. 3A-3 depicts another embodiment of an electrode assembly that may be used in the system of FIG. 2, wherein a disc-shaped contact is shown;

FIG. 3A-4 is a partial cross section view of an electrode of the electrode assembly taken about line 3-3 of FIG. 3A-3;

FIG. 3A-5 depicts another embodiment of an electrode assembly that may be used in the system of FIG. 2, wherein a disc-shaped contact is shown;

FIG. 3A-6 is a partial cross section view of an electrode of the electrode assembly taken about line 5-5 of FIG. 3A-5;

FIGS. 3A-7 to 3A-12 depict various embodiment of an electrode assembly that may be used in the system of FIG. 2, wherein the electrode assembly includes both sensing contacts and stimulating contacts;

FIG. 3A-13 is a partial cross section view of an electrode of the electrode assembly taken about line 13-13 of FIG. 3A-7;

FIG. 3A-14 is a partial cross section view of an electrode of the electrode assembly taken about line 14-14 of FIG. 3A-11;

FIG. 3A-15 is a partial cross section view of an electrode of the electrode assembly taken about line 15-15 of FIG. 3A-9;

FIGS. 4A-4C are partial cross section views of an electrode of the electrode assembly taken about line 4-4 of FIG. 3A-1;

FIGS. 5A-5I illustrate various embodiments of the electrode assemblies that may be used with the system of FIG. 2;

DETAILED DESCRIPTION

Figure 1A:
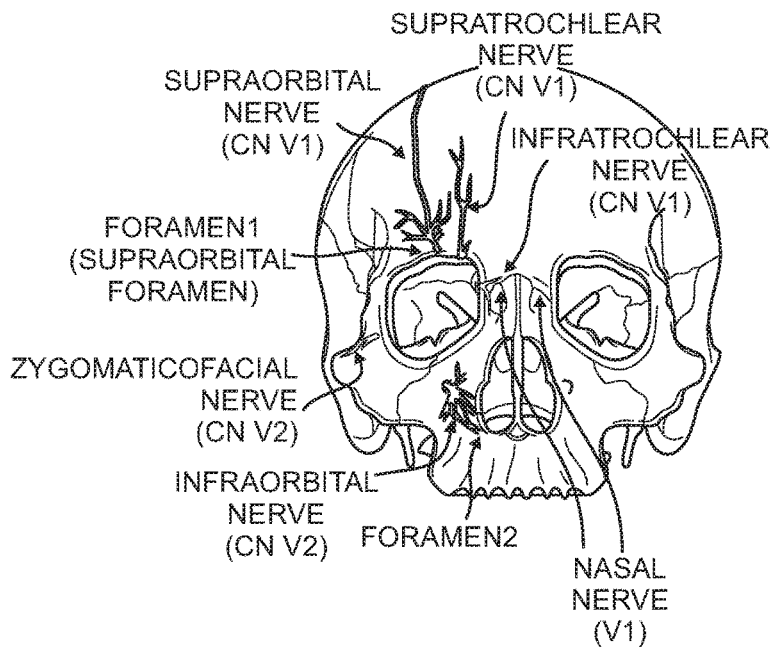
FIGS. 1A and 1B illustrate the location of several branches (nerves) of the trigeminal nerve and the location of the major foramina for the superficial branches of the trigeminal nerve.
Figure 1B:
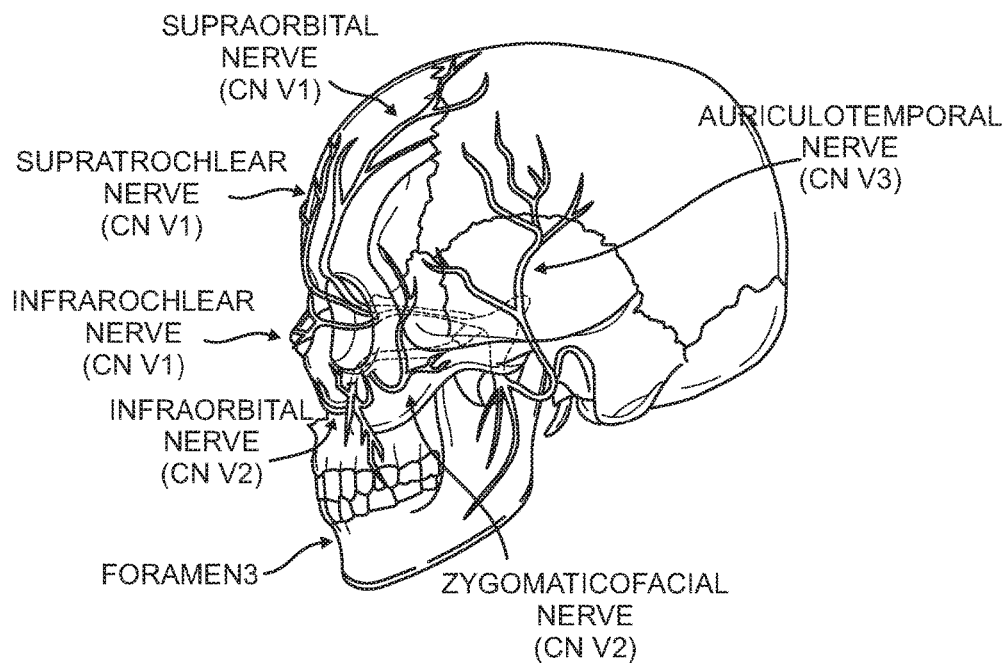

To better appreciate the features of the implantation techniques discussed herein, a brief review of the trigeminal nerve and the subcutaneous and connective tissue of the human head that overlies the trigeminal nerve is now provided. With reference to FIGS. 1A and 1B, the trigeminal nerve is the largest cranial nerve and has extensive connections with the brainstem and other brain structures. The trigeminal nerve, also named the fifth cranial nerve or "CN V," has three major sensory branches over the face, all of which are bilateral, and highly accessible. The supraorbital nerve, or ophthalmic nerve, is frequently referred to as the $V_1$ division. The infraorbital branch or maxillary nerve is commonly referred to as the $V_2$ division. The mentalis branch of the mandibular nerve is referred to as the $V_3$ division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the skin of the lower face (e.g. jaw and tongue) and lips.

These branches exit the skull through three foramina, as shown in FIGS. 1A and 1B. The supraorbital nerve exits at foramen 1, approximately 3.1-3.8 cm from the nasal midline (in adults), and is located immediately above the orbital ridge that is located below the eyebrow. The infraorbital branch or maxillary nerve exits at foramen 2, approximately 2.4-3.0 cm from the nasal midline (in adults) and the mentalis nerve exits at foramen 3, approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus, and then project to the cerebral cortex. Light touch sensory fibers are large myelinated fibers, which ascend to the ventral posterior lateral (VPL) nucleus of the thalamus, and also project to the cerebral cortex. Afferent sensory fibers project from the trigeminal nuclei to the thalamus and the cerebral cortex.

Figure 1C:
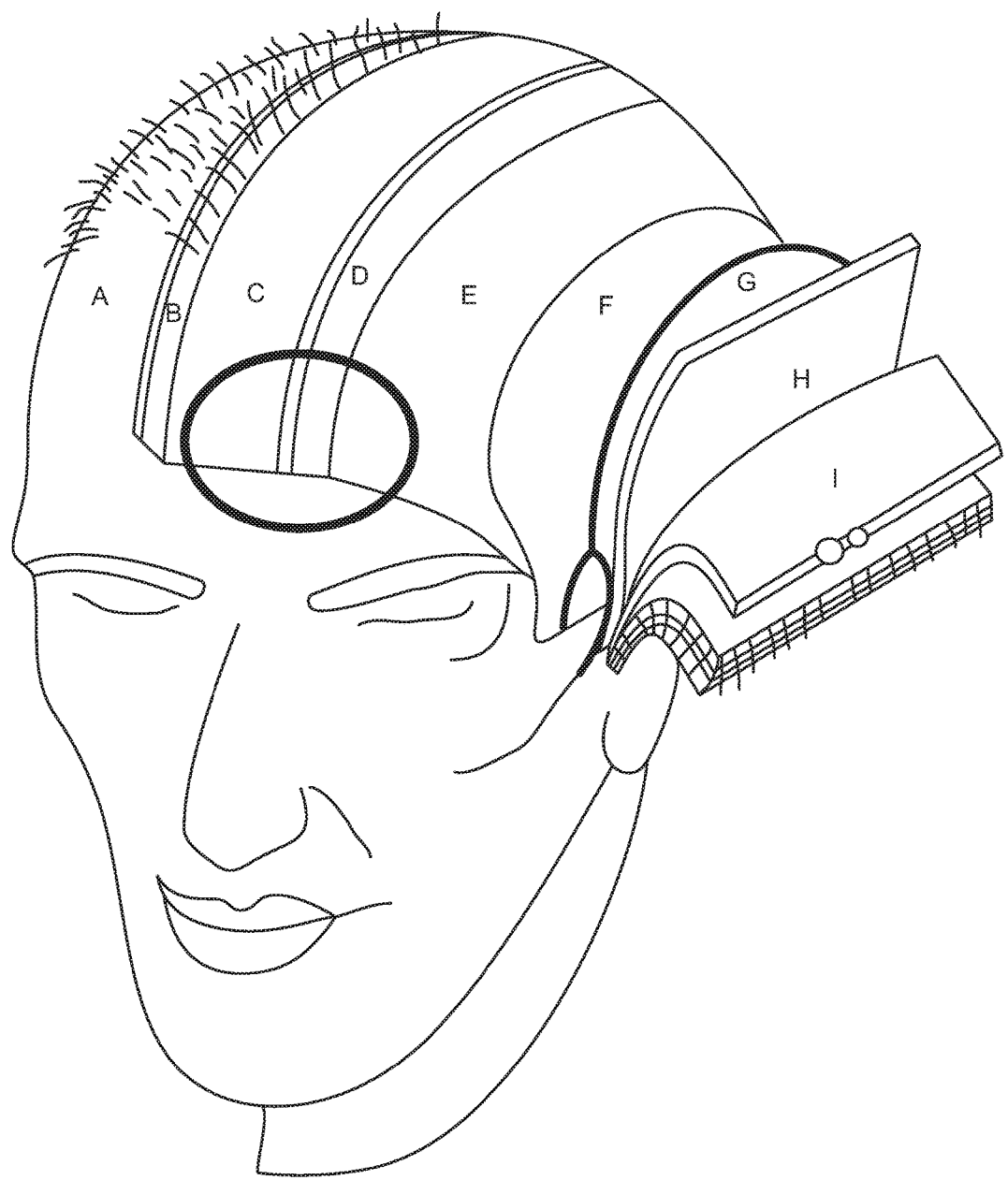
FIG. 1C illustrates various tissue layers of a human head that overlies the trigeminal nerve.

FIG. 1C illustrates, among other layers, the subcutaneous or connective tissues above the periosteum D or pericranium (a membrane that lines the outer surface of the skull) and below the epidermis A (the outermost layer of skin) Also shown is the frontalis muscle C and the associated aponeurosis Loose connective tissue separates the aponeurosis and the frontalis muscle from the periosteum.

In one aspect, the systems and methods disclosed herein may be used in the application of trigeminal nerve stimulation to treat medical disorders including, but not limited to, neuropsychiatric disorders such as depression and major depressive disorder, neurological disorders such as epilepsy and drug resistant epilepsy, cardiac related disorders, fatigue, tinnitus and other medical disorders as may be disclosed in copending application nos. U.S. patent application Ser. No. 12/898,685, filed Oct. 5, 2010 and entitled Extracranial Implantable Devices, Systems and Methods for the Treatment of Neuropsychiatric Disorders; U.S. patent application Ser. No. 12/898,696, filed Oct. 5, 2010 and entitled Extracranial Implantable Devices, Systems and Methods for the Treatment of Neurological Disorder; and PCT International Application No.: PCT/US2011/065003, filed Dec. 14, 2011 and entitled Extracranial Implantable Devices, Systems and Methods for the Treatment of Medical Disorder, all of which are hereby incorporated by reference. Stimulation of peripheral and cutaneous branches of the trigeminal nerve in the face, ear or scalp can be applied and stimulated at safe frequencies, pulse durations and amplitudes. Such treatment and prevention is advantageous over the currently used pharmacological approaches which often have undesirable side effects or lack specificity in their actions.

For a discussion of certain embodiments of implantable electrode assemblies according to aspects of the present disclosure, reference is now made to FIGS. 2-6C, which show various embodiments of the system and electrode assemblies that may be used for the subcutaneous stimulation of the superficial branches of the trigeminal nerve, spinal nerves and other peripheral nerves and methods of fixation of the same.

Figure 2:
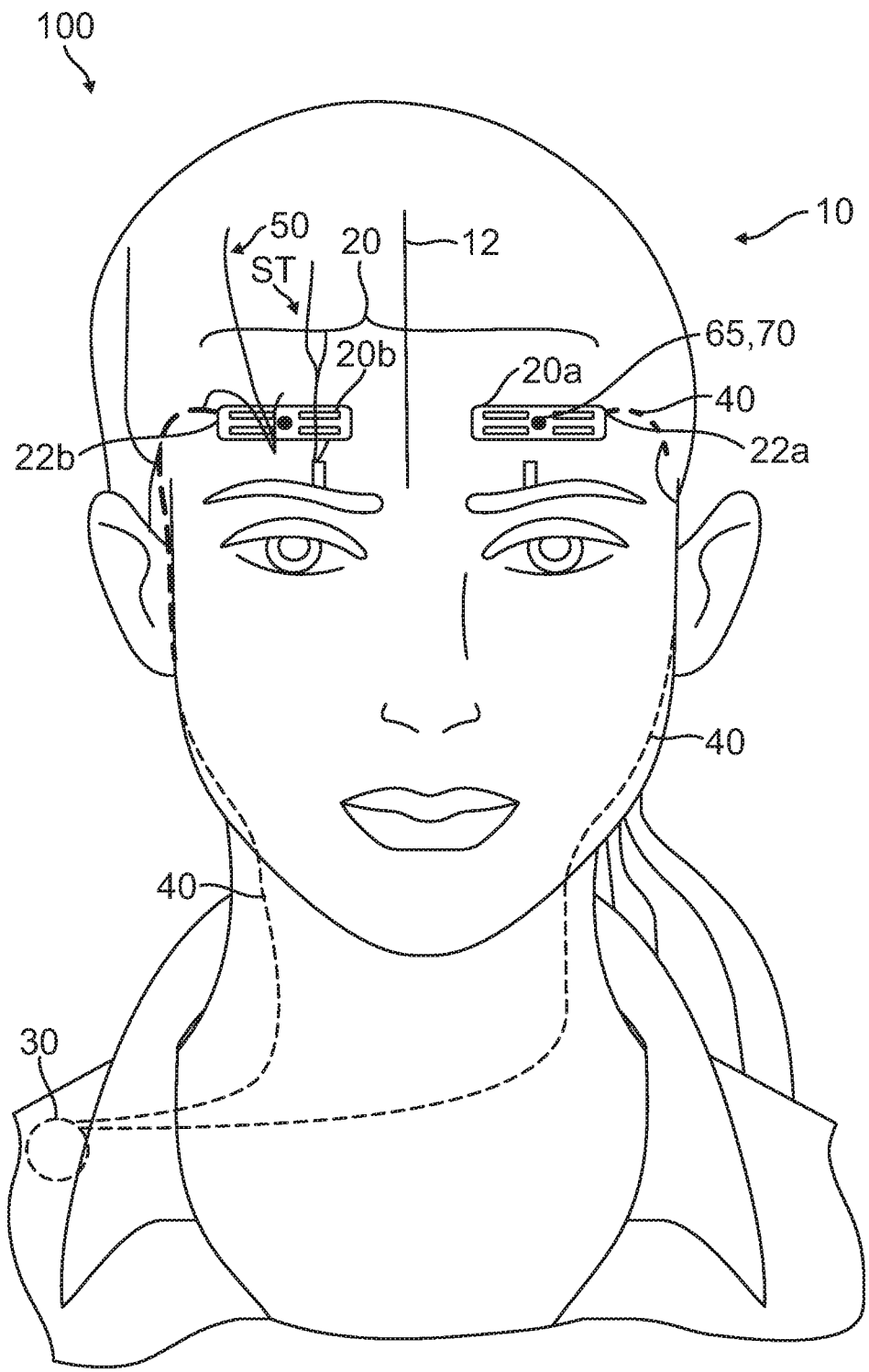
FIG. 2 depicts a patient implanted with an embodiment of an electrode system according to aspects of the present disclosure.

In one embodiment, and as can be understood from FIG. 2, a system 100 for the subcutaneous stimulation of the superficial branches of the trigeminal nerve which may be implanted in a patient 10 includes an electrode assembly 20, a neurostimulator or pulse generator 30, an electrical cable or lead wire 40 to electrically couple the electrode assembly with the pulse generator, and an anchoring device 70 received in a corresponding aperture 65.

The pulse generator 30 may be any type of appropriate signal generating device for neurostimulation. In some embodiments, the pulse generator 30 may include electronic circuitry for receiving data and/or power from outside the body by inductive, radio-frequency (RF), or other electromagnetic coupling. In some embodiments, electronic circuitry includes an inductive coil for receiving and transmitting RF data and/or power, an integrated circuit (IC) chip for decoding and storing stimulation parameters and generating stimulation pulses, and additional discrete electronic components required to complete the electronic circuit functions, e.g. capacitor(s), resistor(s), transistor(s), coil(s), and the like.

In other embodiments, the pulse generator 30 may include a programmable memory for storing a set(s) of data, stimulation, and control parameters. Among other things, memory may allow stimulation and control parameters to be adjusted to settings that are safe and efficacious with minimal discomfort for each individual. Specific parameters may provide therapeutic advantages for various medical disorders. For instance, some patients may respond favorably to intermittent stimulation, while others may require continuous stimulation to treat their symptoms.

In some embodiments, the pulse generator 30 may include a power source and/or power storage device. Possible options for providing power to the system include but are not limited to: an external power source coupled to pulse generator 30, e.g., via an RF link, a self-contained power source utilizing any suitable means of generation or storage of energy (e.g., a primary battery, a replenishable or rechargeable battery such as a lithium ion battery, an electrolytic capacitor, a super-capacitor, a kinetic generator, or the like), and if the self-contained power source is replenishable or rechargeable, means of replenishing or recharging the power source (e.g., an RF link, an optical link, a thermal link, an inductive link, or other energy-coupling link).

In some embodiments, pulse generator 30 operates independently from other devices. In other embodiments, pulse generator 30 operates in coordination with other implanted device(s) or other device(s) external to the patient's body. For example, a pulse generator may communicate with other implanted neurostimulators, other implanted devices, and/or devices external to a patient's body via, e.g., an RF link, an ultrasonic link, a thermal link, an optical link, or the like. Specifically, pulse generator 30 may communicate with an external remote control (e.g., patient and/or physician programmer) that is capable of sending commands and/or data to a neurostimulator and that may also be capable of receiving commands and/or data from a neurostimulator.

The system 100 and/or the electrode assembly 20 may be part of a kit. In some embodiments, the kit may also include instructions for implantation according to a method disclosed herein. In some embodiments, the kit may also include instructions for monitoring the clinical effects of the stimulation to achieve proper adjustment of stimulation parameters and system configuration.

In some embodiments, the system may utilize a closed loop design and may include a closed loop device or sensing device. In such a system, the closed loop device may include the stimulating electrode or additional set of electrodes, indwelling catheters, or cutaneous or implantable physiologic monitors. The device may be configured to detect brain activity, heart rate, pulse oximetry, cerebral blood flow, systolic, diastolic blood pressure, or mean arterial pressure, transcranial Doppler, cardiac parameters (ejection fraction, pulmonary, atrial, or ventricular pressures), heart rate variability (using time, frequency, or non-linear or other measures of heart rate variability), mechanical motion one or more axial directions, the presence of molecules that could signify a potentially-dangerous condition or the achievement of a desired clinical effect, or other physiologic parameters to provide self-tuning adaptive feedback control for the neurostimulator including, but not limited to, fuzzy controllers, LQG (linear-quadratic-gaussian) controllers and artificial neural networks (ANN). Adaptive learning controllers can learn from the previous response of a particular patient or similar patients to stimulation settings which helped alleviate conditions being treated. In some embodiments, this qualitative and/or quantitative feedback may be used by the system to automatically or otherwise adjust the stimulation parameters in a closed-loop fashion to optimize the clinical effects of the stimulation.

In some embodiments, such as the embodiments shown in FIGS. 2-5I, the neurostimulation may be provided using an electrical neurostimulator and the system is configured to deliver a charge density significantly less than 10 $\mu C/cm^2$ at a current density below 25 $mA/cm^2$. In one embodiment, the output current is 3 mA at 250 $\mu sec$, with an electrode radius of 0.2 cm and, therefore, the charge density is 0.59 $\mu C/cm^2$.

In some embodiments, the electrode assembly 20 may be electrically coupled to an external neurostimulator wirelessly, with transfer of energy across the skin by inductive coupling between a coil implanted in the patient and a coil in the external pulse generator. There would of course be no implanted signal generator 30 in such embodiments. As an additional alternative, the electrode assembly 20 may be implanted but the pulse generator is located externally, and the electrical cables 40 electrically couple the implanted electrodes with the external pulse generator. The pulse generator itself may be placed in a variety of locations under the skin, such as pectorally, and the leads placed under the skin of the patient to connect the pulse generator and the electrode assembly.

FIG. 2 illustrates an embodiment of an electrode assembly 20 that may be used in the system 100. The electrode assembly 20 may comprise two implanted electrodes 20a and 20b which are placed at, near or adjacent to the supraorbital foramina, located over the orbital ridge approximately 3.1 to 3.8 cm lateral to the nasal midline in adults. In some embodiments, the electrode assembly is configured for placement at the supraorbital foramen to stimulate both the supraorbital and supratrochlear branches so as to have a pair of contacts positioned approximately where the supraorbital nerve exits the supraorbital foramen above the eye at an average of 32 mm from midline and also a pair of contacts positioned where the supratrochlear nerve exits the foramen at an average of 22 mm from midline. As shown in FIG. 2, the lateral ends 22a and 22b of the electrodes 20a and 20b (respectively) is where each electrode body connects or couples to leads or lead wires 40 for conveying the electrical stimuli from the pulse generator 30. The pulse generator 30 itself may be placed in a variety of locations under the skin, such as pectorally, and the leads placed under the skin of the patient to connect to the pulse generator. Alternatively, as discussed above, the pulse generator 30 may be external to the body.

Figures 3, 3A:
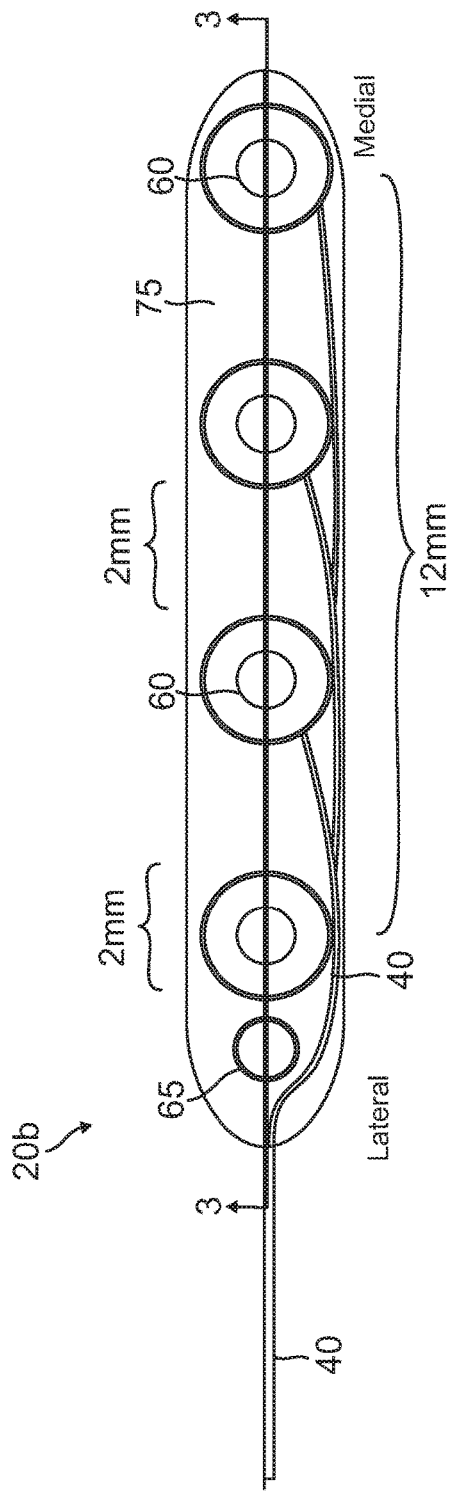
Figures 3, 3A, 4:
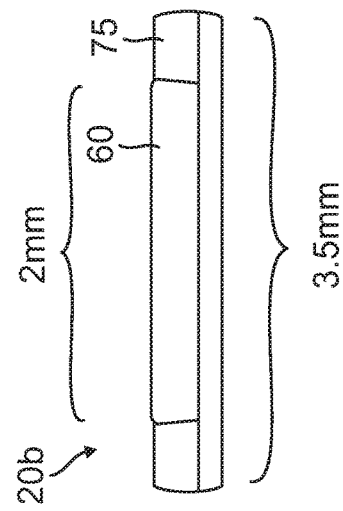
Figures 3, 3A, 4, 5, 6, 7:
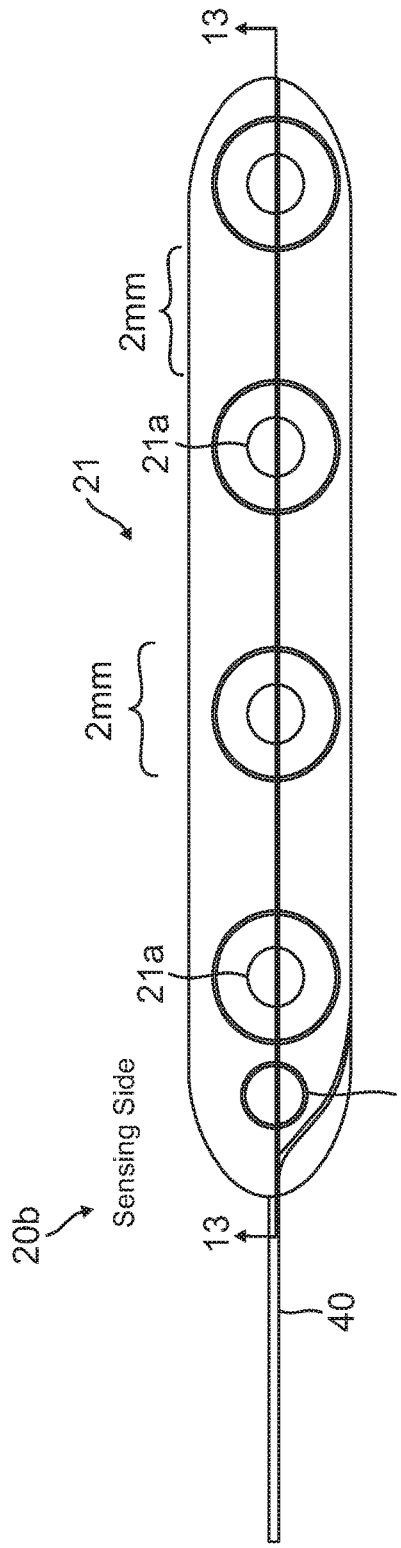
Figures 3, 3A, 4, 5, 6, 7, 8:
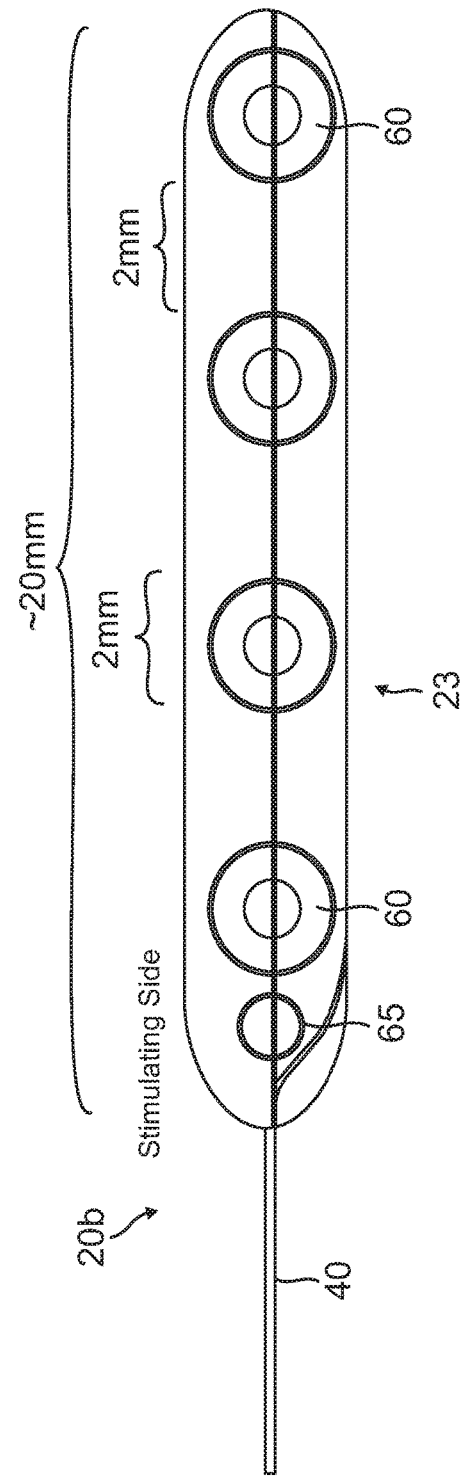
Figures 3, 3A, 4, 5, 6, 7, 8, 9:
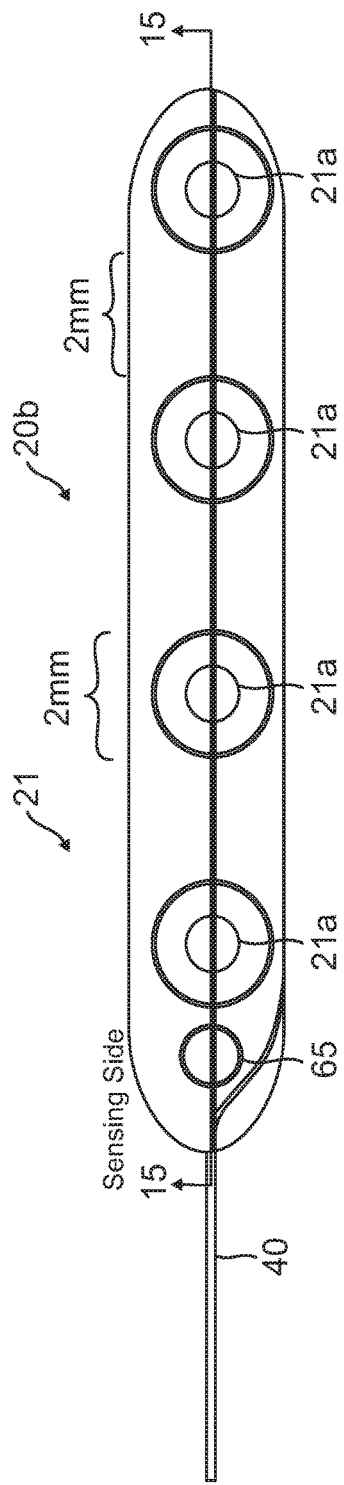
Figures 3, 3A, 4, 5, 6, 7, 8, 9, 10:
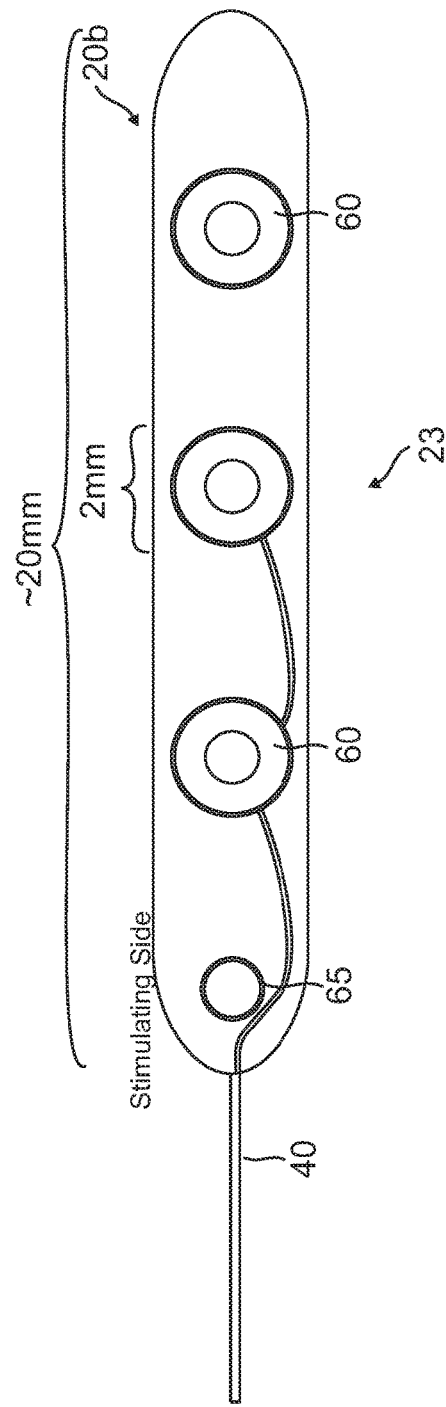
Figures 3, 3A, 4, 5, 6, 7, 8, 9, 10, 11:
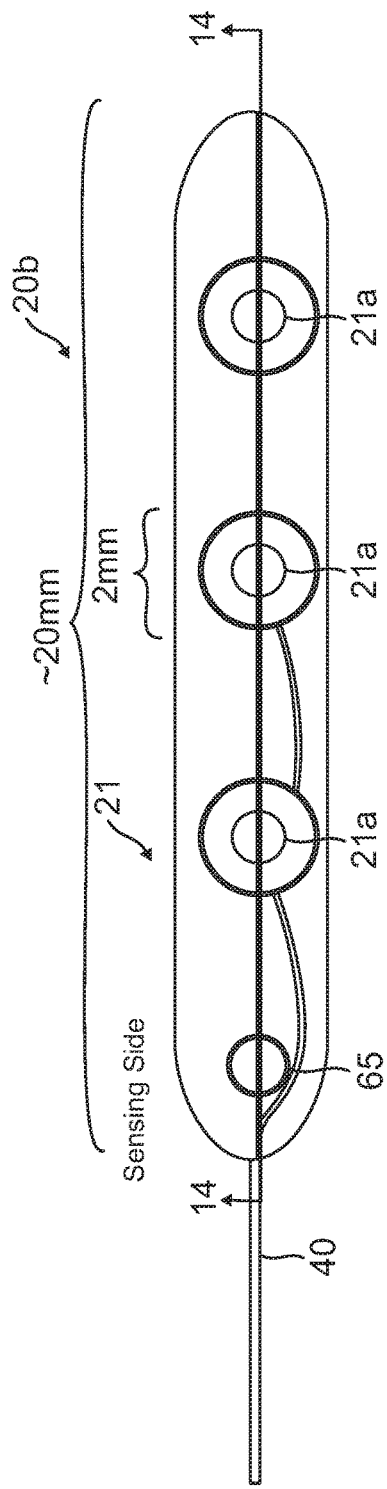
Figures 3, 3A, 4, 5, 6, 7, 8, 9, 10, 11, 12:
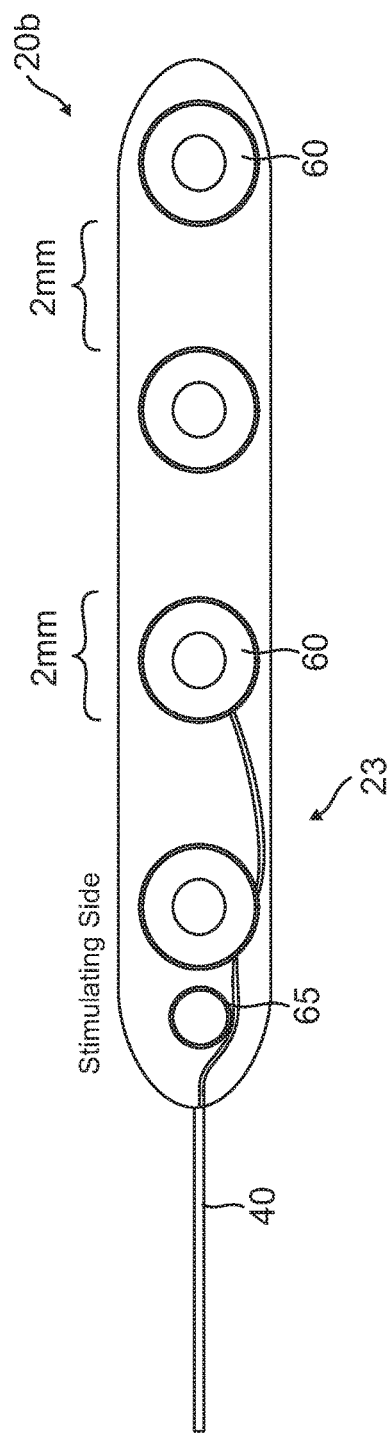

In one embodiment, and as illustrated in FIGS. 3A-1 to 3A-6, and with reference to FIG. 2, each electrode body such as electrode body 20a includes at least one contact 60 and at least one aperture 65 configured to accept an anchoring device 70 and insulating areas 75. The electrode body 20a may be a paddle or a plate or other appropriate shape. Various shapes for the contacts 60 may be implemented. For example, contacts 60 may be rectangular as shown, for example, in FIGS. 3A-1, 3A-2, or may be disc-shaped as shown in FIGS. 3A-3, 3A-5, and 3A-7 through 3A-12. As shown in FIG. 3A-5, an electrode may have a thickness of less than 1 mm and include a pair of contacts 60 each comprising a platinum/iridium disk 4 mm in diameter with a center-to-center distance of 10 mm. As shown in FIG. 3A-3, an electrode may have a thickness of 1 mm and include four contacts 60 each comprising a platinum/iridium disk 2 mm in diameter with a lateral center-to-medial center distance of 12 mm, a contact-to-contact distance of 2 mm. In other embodiments, the diameter of the disc shaped contact may be less than 2 mm, or 3 mm, or greater than 4 mm. In other embodiments, such as that shown in FIG. 2 and FIGS. 5A-5H, the contacts may be elongated rectangular bodies with rounded corners or other shaped bodies, preferably with rounded corners. Such shapes avoid "hot spots" in the electrical field that may be generated by sharp angular corners. The electrode body 20a and 20b and/or the contact points 60 may be made of a noble or refractory metal or compound, such as titanium, titanium nitride, platinum, iridium, tantalum, niobium, rhenium, palladium, gold, nichrome, stainless steel, or alloys of any of these, in order to avoid corrosion or electrolysis which could damage the surrounding tissues and the assembly. In various embodiments, the body 20a and 20b may have a thickness of 7 mm, 5 mm, 1 mm or less than 1 mm. The relative thinness of the electrode body may help to improve the cosmetic appearance of the electrode body at/under the forehead of the patient. In one embodiment, the body may have a length Y of 8 cm and width X of 5 mm. In various embodiments, the length Y may be between 1 mm and 10 cm and the width X may be between 5 mm and 10 cm. For brevity, the terms "electrode" and "electrode body" are used interchangeably herein.

As shown in FIG. 2 and FIG. 3A-1, the electrode 20a may be a bipolar electrode and include two pairs of contacts including a first pair of conductive contacts 60a and 60b configured for stimulation of a first region, such as the supratrochlear nerve (see FIG. 1A) and a second pair of conductive contacts 60c and 60d configured for stimulation of a second region, such as the supraorbital nerve (see FIG. 1A). Each pair of contacts is thus configured for an antidromic stimulation of the corresponding nerve. In other words, each pair of contacts is positioned overlaying the same nerve such that the current induced between the contacts travels in the nerve fiber direction. Such fiber-directed current excitation can also be induced by a pair of contacts that have a lateral extent so as to excite both the supraorbital and the supratrochlear nerves. For example as shown in FIG. 3A-2, the electrode 20a may be a bipolar electrode and include a first contact 60e configured for stimulation of the supratrochlear nerve and the supraorbital nerve in a first region, and a second contact 60f configured for stimulation of the same supraorbital nerve and supraorbital nerve but in a second region. As discussed in more detail below, and with reference to FIG. 2 and others, an electrode assembly 20 may include electrodes 20a and 20b configured for the bilateral simultaneous and asynchronous stimulation of the ophthalmic nerves, its branches and/or other nerves as described herein. In other embodiments, the electrode assembly 20 may include only an electrode 20a, thereby delivering unilateral stimulation to the ophthalmic nerve, its branches and/or other nerves as described herein. While the electrode assembly 20 is shown in FIGS. 2, 3A-1 and 3A-2, and others, with pairs of electrical contacts (60a/b, 60c/d, 60e/f), in other embodiments, there may be a greater or lesser number of contacts on each of the bodies 20a, 20b.

In addition to stimulating electrodes, some electrode contact elements can be used for sensing as well as stimulating, or additional contacts may be integrated into the electrode assembly 20 to provide dedicated conductive areas for sensing (e.g., brain electrical activity). In some embodiments, the electrode assembly may include a dual function sensing-stimulating electrode. For example, and as shown in FIGS. 3A-7 to FIG. 3A-15, the electrode body 20a and 20b may include a sensing side 21 having sensing contacts 21a and a stimulating side 23 having stimulating contacts 60. The sensing side faces the frontal bone portion of the forehead whereas the stimulating side faces the ophthalmic nerves. As can be understood from the partial cross section view of FIG. 3A-13, the contacts 21a and 60 may be aligned or directly opposed to each other. In other embodiments, and as can be understood from the partial cross section views of FIGS. 3A-14 to 3A-15, the contacts 21a and 60 may be at least partially offset from each other.

In other embodiments, the electrode assembly may be configured for sensing only or the assembly may include one or more electrode bodies configured for sensing and/or stimulation. For example, in the context of epilepsy, most seizures are known to originate in the frontal and temporal lobes. In one embodiment, an electrode body having a sensing side with sensing contacts is placed under the frontalis in the forehead region (see e.g. FIG. 5A) and/or under the temporalis in the temporal region (see FIG. 5J). In either location, the electrode body is located in the loose connective tissue between the muscle and the underlying periosteum. Advantageously, securing the sensing electrodes to the bone and/or the periosteum underneath the soft tissue facilitates the resolving ability of the sensing electrode to detect seizures and/or other brain activities indicative of neuropsychiatric pathology or normal brain activity. For example, if a patient is known to have seizures originating from the temporal lobes bilaterally (mesial temporal sclerosis) then a sensing array (electrode body/assembly) is placed on the bone over the temporal lobes bilaterally (see e.g. FIG. 5J). Once seizure activity is detected, the sensing electrode body/assembly will communicate with one or more stimulating electrode assembly and trigger trigeminal nerve stimulation. In embodiments where a dual sensing/stimulating electrode assembly is used, the sensing side will detect seizure activity and the stimulating side will stimulate the trigeminal nerve (or a respective branch) (e.g. the auriculotemporal nerve shown in FIG. 5J)

As can be understood from FIGS. 4A-4C, which illustrate cross section views of an electrode body 20a, in some embodiments, the electrical contacts 60a, 60c may be flush with the insulating areas 75 of the electrode body 20a. In some embodiments, the contacts 60a, 60c may be in a raised position relative to the insulating areas 75 of the electrode body 20a. In some embodiments, the contacts 60a, 60c may be in a recessed position relative to the insulating areas 75 of the body 20a.

Figure 3B:
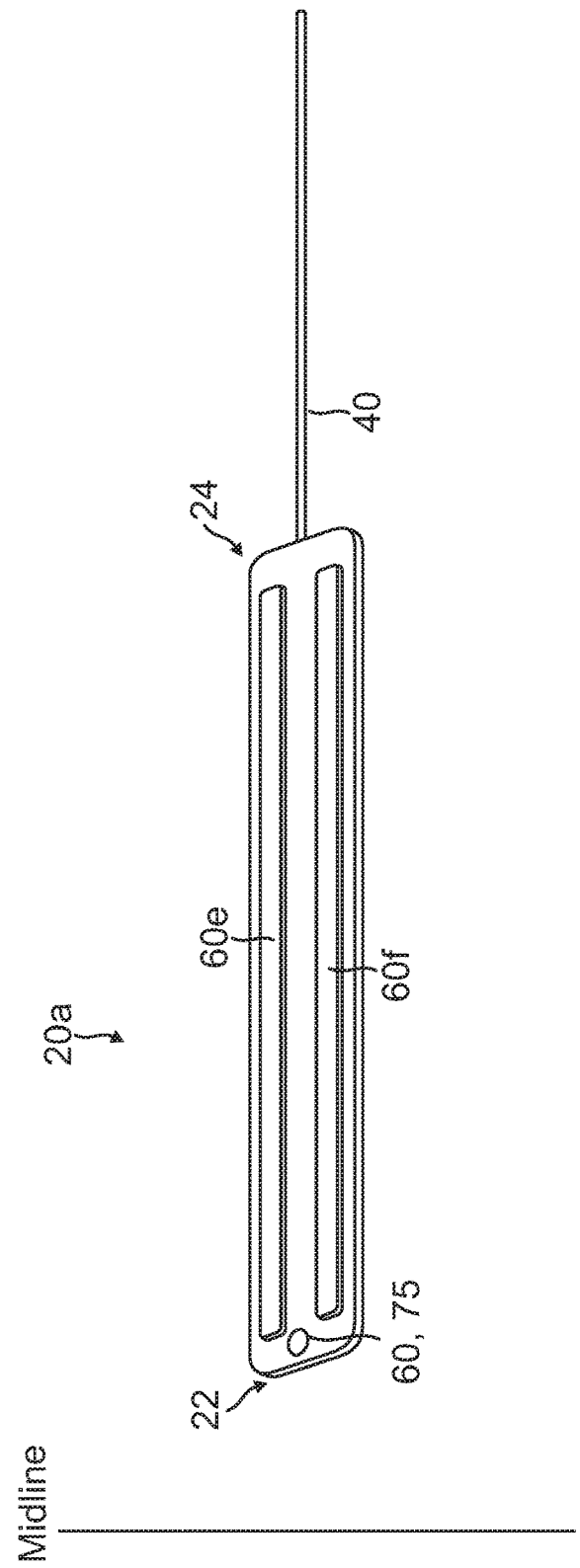
FIGS. 3B-3C depict embodiments of an electrode assembly that may be used in the system of FIG. 2, wherein an alternative anchoring position is shown.
Figure 3C:
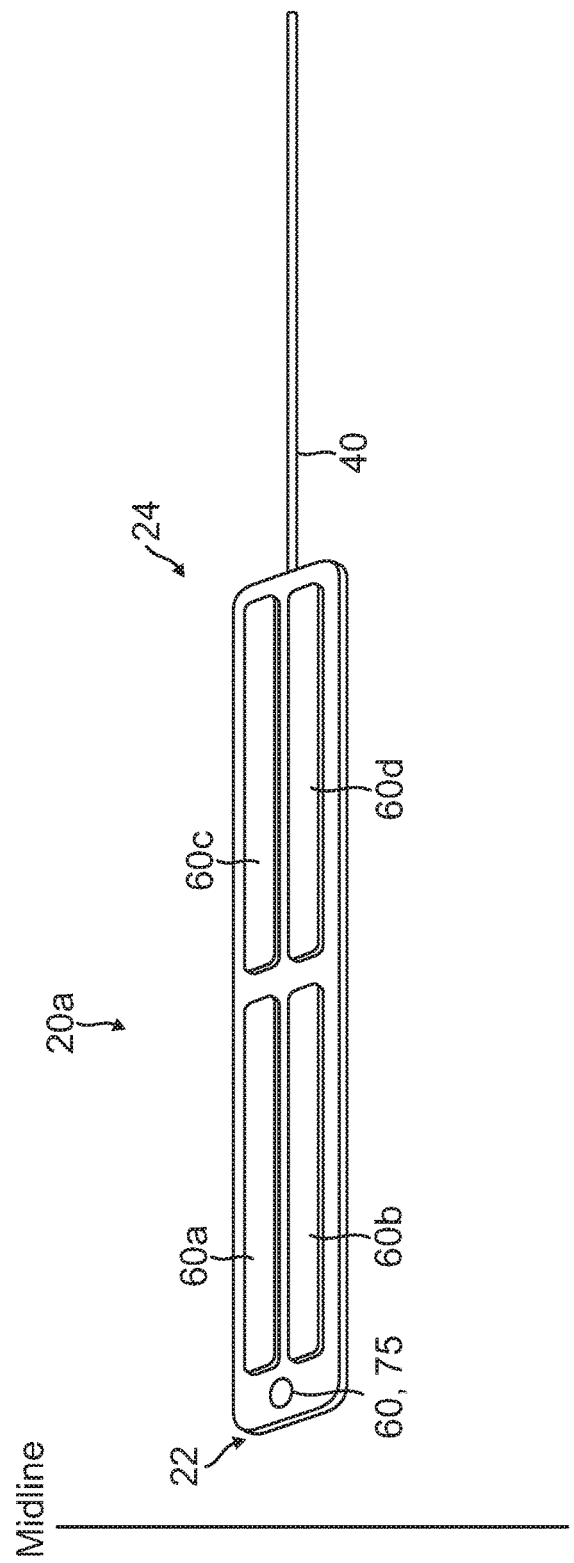

The electrode body may further comprise an aperture 65 for receiving an anchoring device 70. Once the electrode body is placed at the desired location in the loose connective tissue between muscle and the periosteum (or a vertebra), an anchoring device 70 is introduced into the aperture to secure the electrode body at the desired location. By securing the electrode to the bone, lead migration and electrode movement are minimized. The anchoring device 70 may be a screw, such as a self tapping screw, a pin, an expandable rivet, a solidifying adhesive material, or other appropriate anchoring device. While the aperture 65 and corresponding anchoring device 70 is shown generally at the center of the body 20a and approximately equidistant between the contacts 60, it can be appreciated that the aperture 65 and corresponding anchoring device 70 may be located at an end 22 of the body 20a opposite an end 24 where the lead or lead wire 40 is coupled to the body, such as the embodiments shown in FIGS. 3B and 3C. Such end placement may dampen the mechanical motion that is transmitted from the leads to the electrode assembly when the leads are coupled to the body. In other embodiments, the aperture 65 and corresponding anchoring device 70 may be at another location relative to the electrode body, such as at a location that is not at the midline but rather at a corner or at some location between the midline and the edge or corner. In still further embodiments, the body may include more than one aperture (each of which will receive a respective anchoring device) to further aid in securing the body to the bone.

Figure 5A:
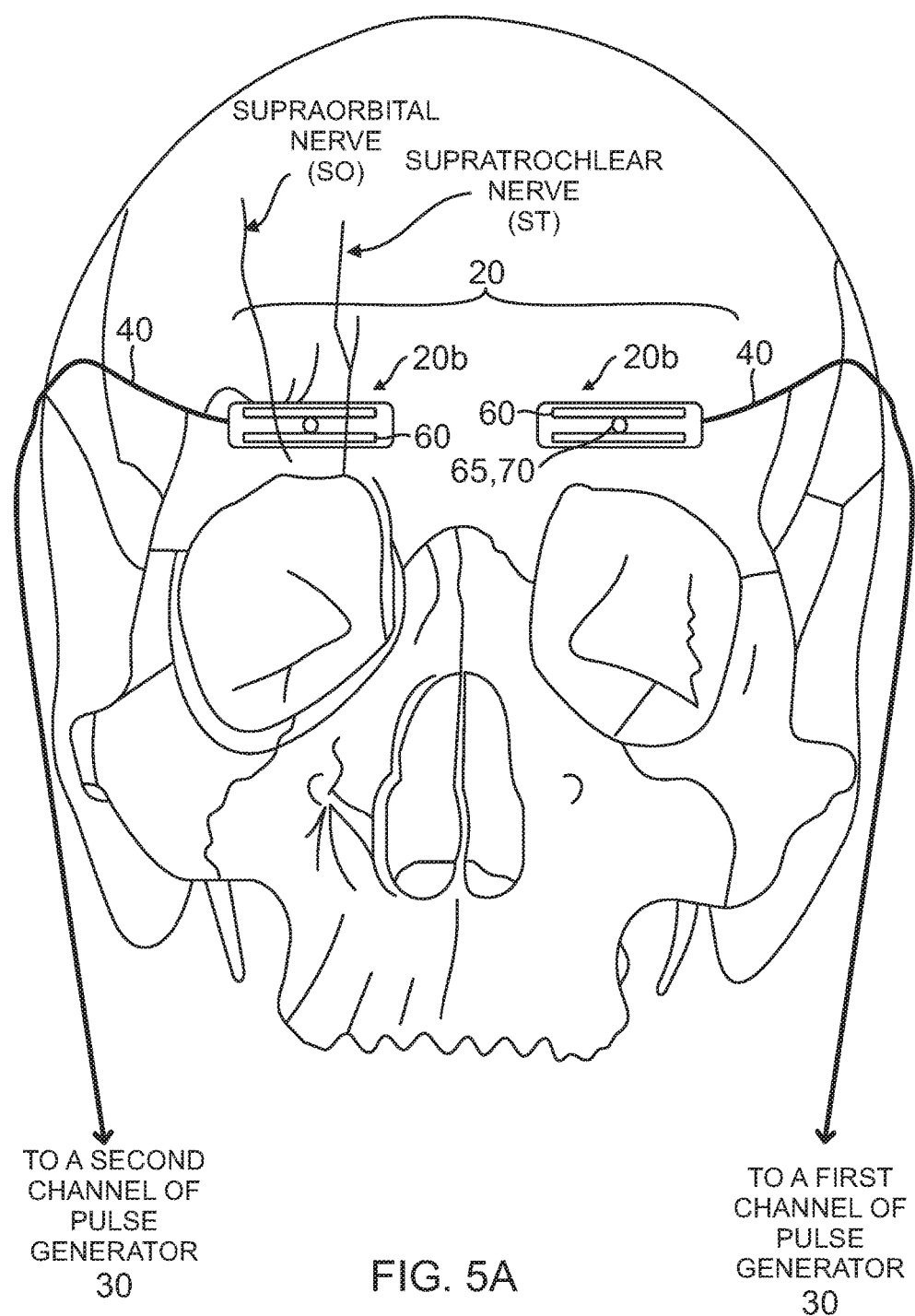
Figure 5B:
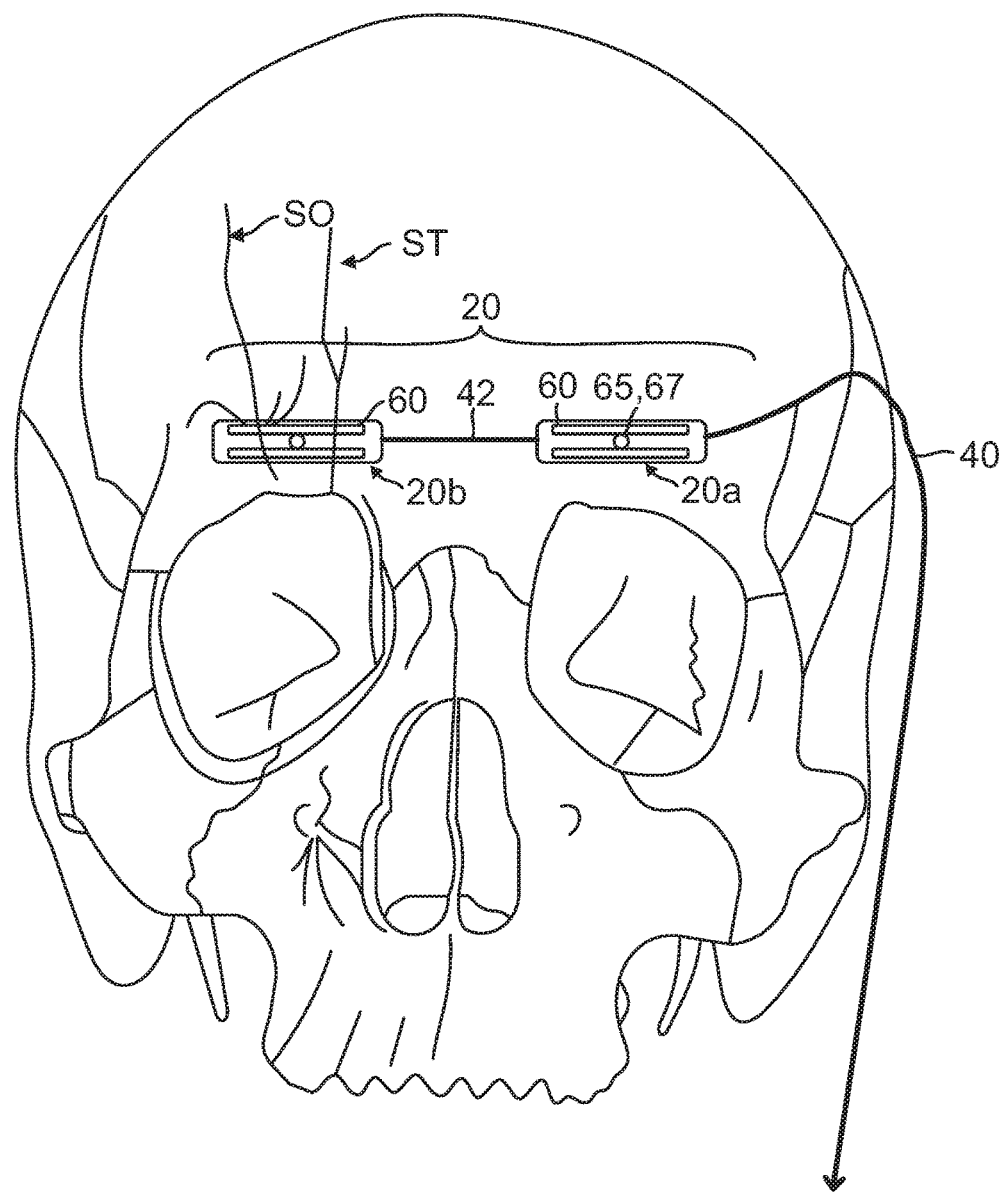
Figure 5C:
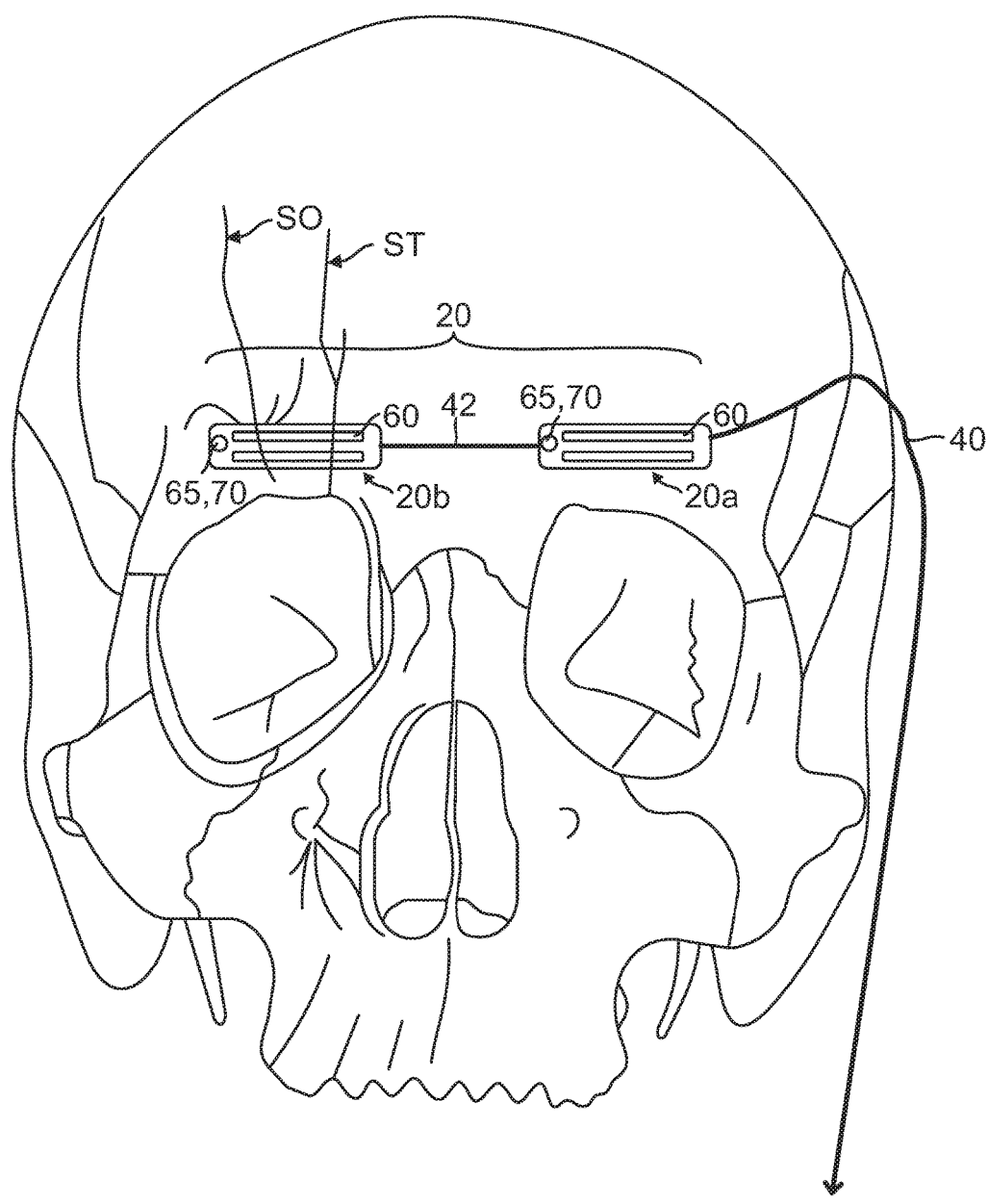

FIGS. 5A-5H illustrate various embodiments of an electrode assembly that may be used with the system 100. In particular, various lead wire configurations and anchoring point configurations are shown. In one embodiment such as shown in FIG. 5A, each electrode 20a and 20b has its own corresponding lead 40. Each electrode includes two contacts 60 and a centered aperture 65 on its midline and corresponding anchoring device 70. Electrode 20a is coupled to a first channel of the pulse generator and electrode 20b is coupled to a second channel of the pulse generator 30, each through an independent lead or cable 40. Alternatively, a single lead 40 may drive both electrodes 20a and 20b as shown in FIG. 5B. Electrode 20a is coupled to electrode 20b in series via connecting lead 42 and the serially connected electrodes are coupled to a first channel of the pulse generator via lead 40. FIG. 5C illustrates a variation of the embodiment of FIG. 5B in that the apertures 65 are located at the distal end of each electrode. The same aperture location is shown in FIG. 5D but where each contact 20a and 20b has its own separate lead 40 analogous to the embodiment of FIG. 5A.

Figure 5E:
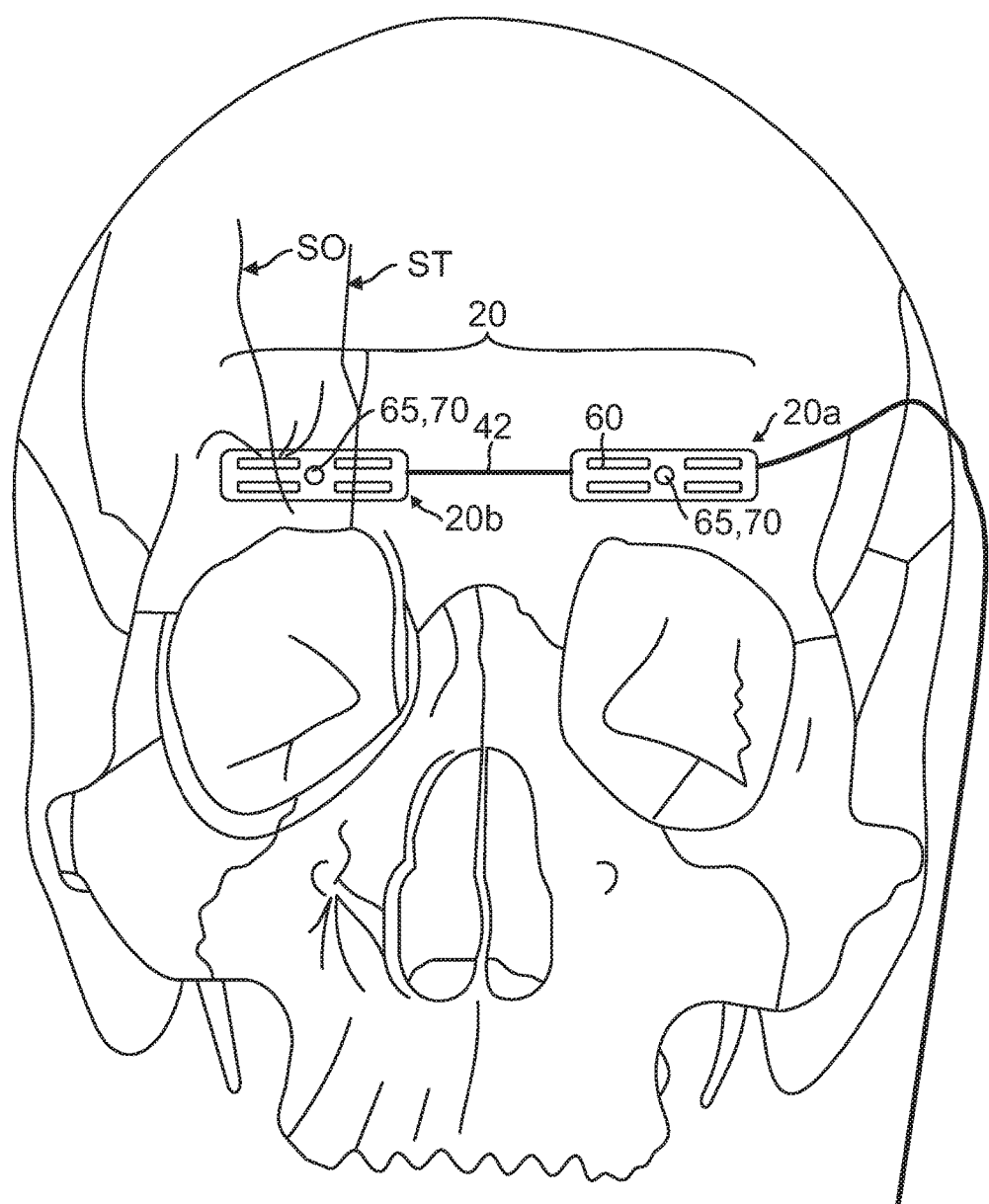
Figure 5F:
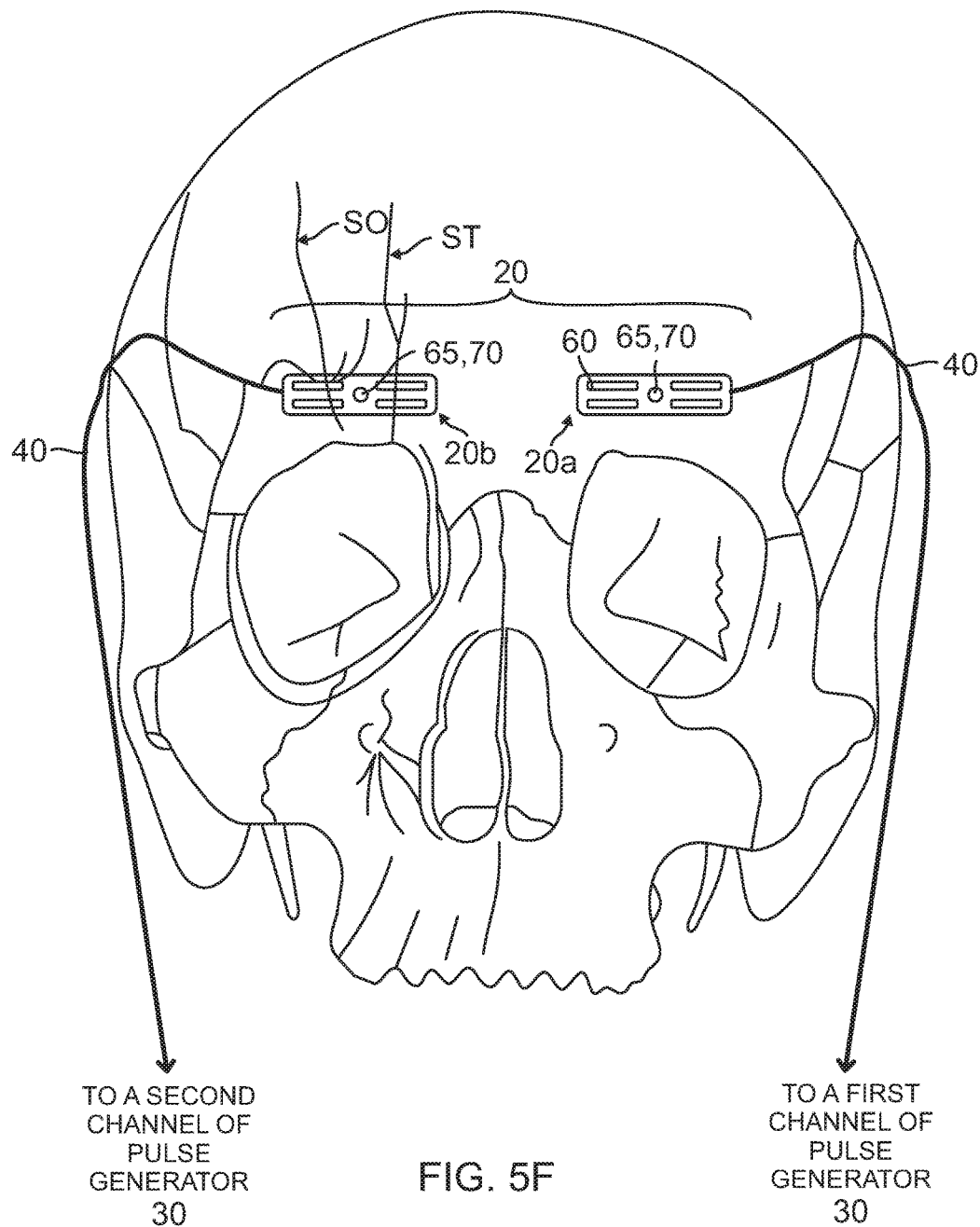
Figure 5G:
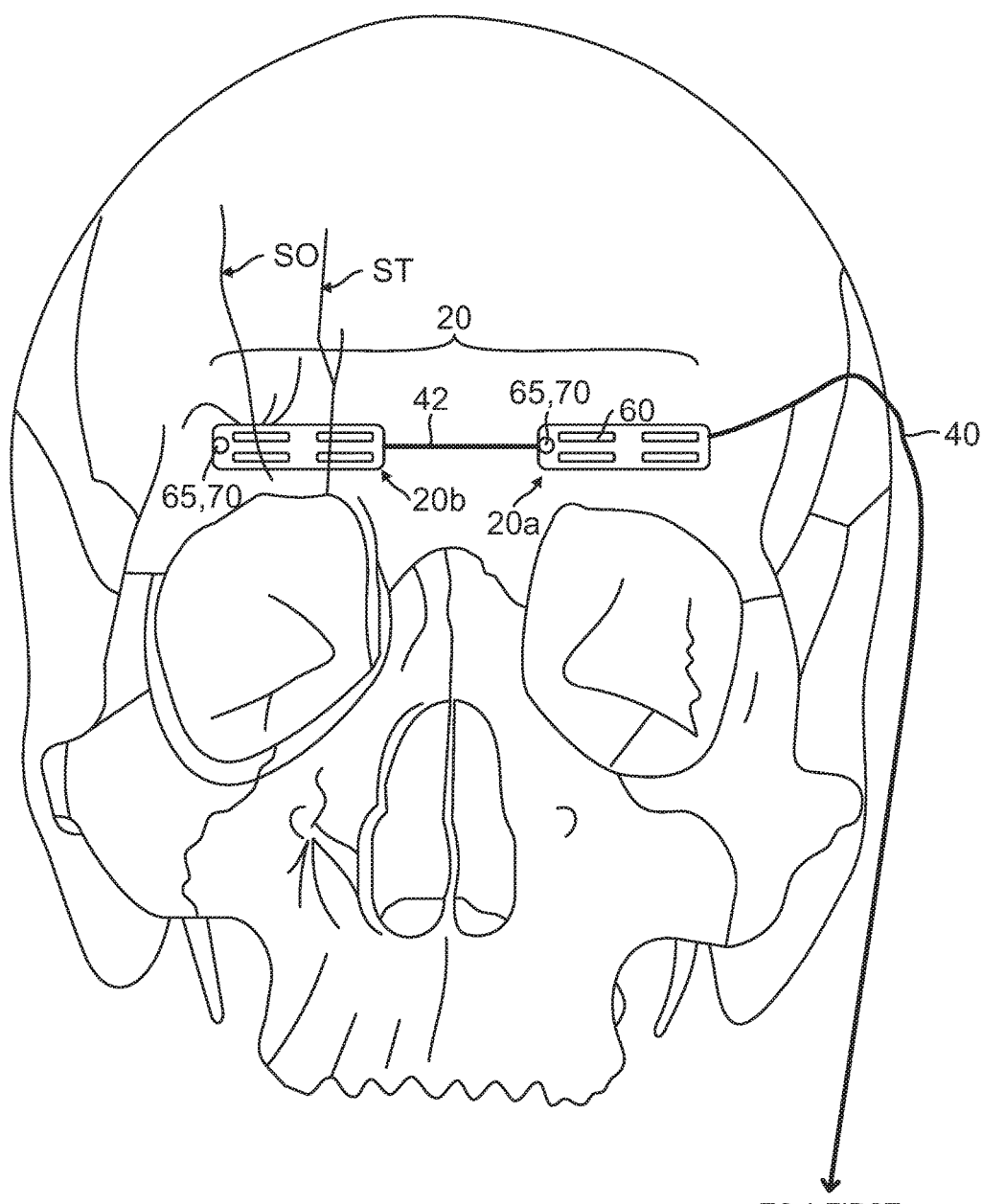
Figure 5H:
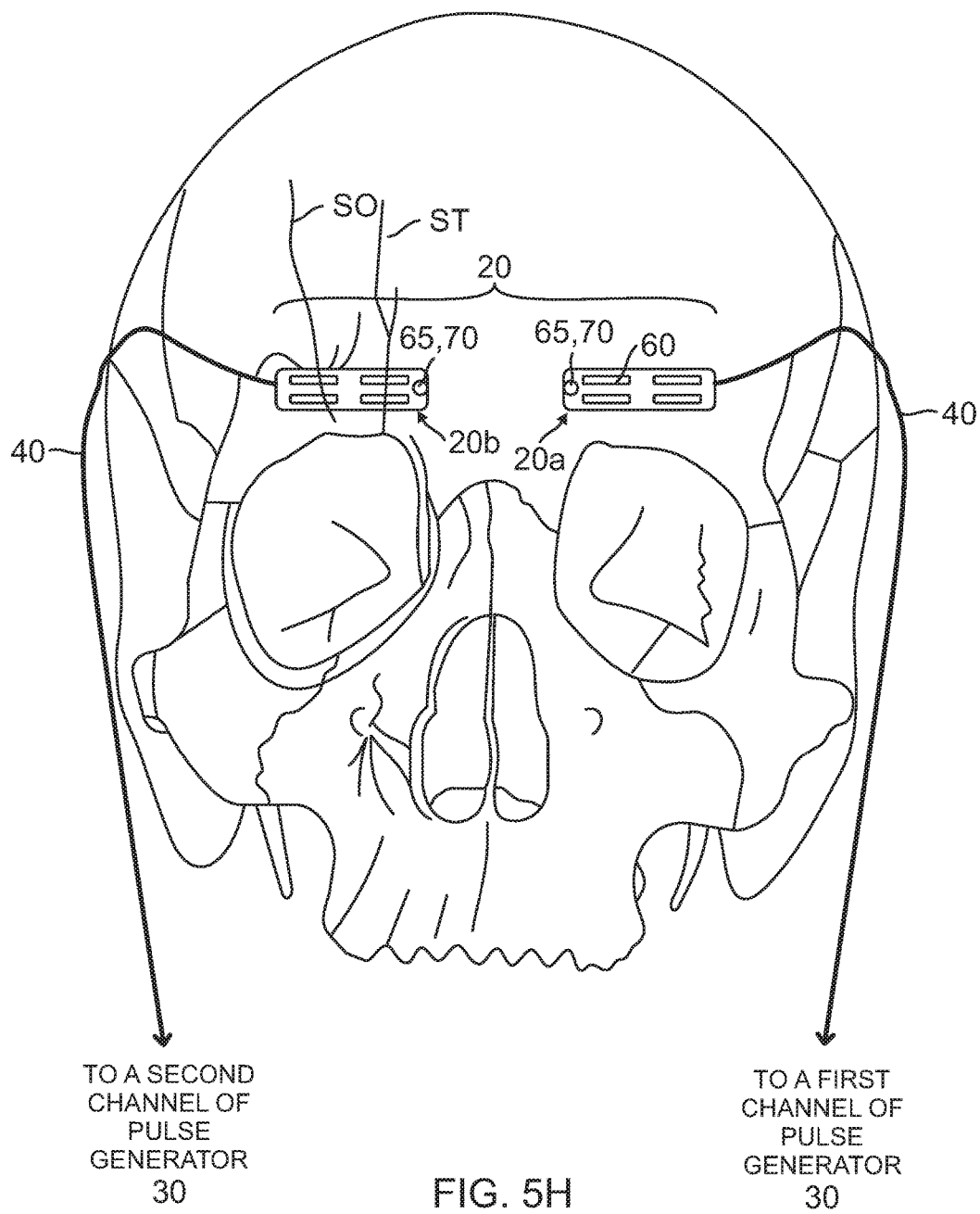

Rather than have a single pair of contacts for both the supraorbital and supratrochlear nerves, each nerve may have its own dedicated pair of contacts 60. In other words, the four embodiments discussed above with regard to FIGS. 5A through 5D may be modified such that each contact 20a and 20b includes four contacts 60. FIG. 5E corresponds to FIG. 5B in that a single lead 40 serves both electrodes and each aperture is centrally located on the midline. Electrode 20a is coupled to electrode 20b in series via connecting lead 42 and the serially connected electrodes are coupled to a first channel of the pulse generator 30. FIG. 5F corresponds to FIG. 5A in that each electrode 20a and 20b has its own dedicated lead 40 and a centered aperture 65 on the midline. Electrode 20a is coupled to a first channel of the pulse generator 30 and electrode 20b is coupled to a second channel of the pulse generator 30, each through an independent lead or cable 40. FIG. 5G corresponds to FIG. 5C in that a single lead 40 serves both electrodes and each aperture is located at the distal end of the electrode on the midline. Electrode 20a is coupled to electrode 20b in series via connecting lead 42 and the serially connected electrodes are coupled to a first channel of the pulse generator 30. Finally, FIG. 5H corresponds to FIG. 5D in that each electrode 20a and 20b has its own dedicated lead 40 but the apertures 65 are located at the distal end of their respective electrodes.

To use, and as can be understood with reference to FIGS. 1C and 2, in one embodiment, a physician identifies the supraorbital foramen via intra-operative fluoroscopy, and makes a small incision in the eyebrow just lateral to the foramen. Once the incision is made, the surgeon dissects through the soft tissue to the periosteum directly above the foramen and inserts the electrode such that the contacts are facing outwards towards the skin (as opposed to inwards towards the brain) and the electrode body is substantially directly against the bone. More specifically, and with reference to FIG. 1C, an electrode body is positioned in the loose areolar tissue so as to overlay the periosteum D but underlay the frontalis muscle C. The contacts face outwards towards the skin. The electrode may then be centered about the supraorbital foramen and secured via an anchoring device inserted through the aperture. By securing the electrode body to the bone, issues related to lead migration and skin irritation are reduced. Because the nerves enervate and associate with the frontalis, the frontalis may be pulled slightly away from the underlying loose areolar tissue such that the supraorbital and supratrochlear nerves will displace with the frontalis muscle. This is quite advantageous as the electrode body may then be inserted into the loose areolar tissue without the danger of transecting or damaging the supraorbital and supratrochlear nerves. Locating the electrode in this manner places the contacts in contact with, near, or adjacent to the nerve without requiring direct attachment to the nerve. The same implantation procedure can be performed on the contralateral side of the patient as well, for bilateral implantation, or may be performed on one side only for unilateral implantation.

Following placement of the electrode assembly, it is then connected to an implanted neurostimulator 30 via the implanted electrical cables 40, which are placed under the patient's skin. In the illustrated embodiment, the stimulation via the neurostimulator 30 is via electrical cables 40. In alternative embodiments, the electrical stimulation can be performed wirelessly, with an external, non-implanted neurostimulator, which uses inductive coupling to deliver energy to the implanted electrode assembly 20. In still other embodiments, the electrode assembly 20 is implanted, while the non-implanted neurostimulator is placed externally, and the two are connected via electrical cables 40.

In other embodiments, the electrode assembly 20 may comprise a plurality of multicontact electrodes which may include a plurality of contacts and a plurality of continuous or discrete insulated regions. In various embodiments, the geometry or layout of the electrode body may be a linear electrode with a single contact or a series or plurality of conductive contacts and insulating spaces, or a flatter, "ribbon" or "strip" electrode, also with the possibility of one or more conductive area(s) and insulated area(s) on the surface (s).

As can be understood from FIG. 2 and others, the electrode assembly 20 is configured to stimulate branches of both the right and left ophthalmic nerves either simultaneously or asynchronously. The placement of the first implanted electrode 20a with contact pairs 60 and the second electrode 20b with contact pairs 60 on opposite sides of the nasal midline 12 assures that stimulation current is fiber-directed or in the direction of the afferent ophthalmic or supraorbital nerve. Furthermore, this configuration of the electrode assembly 20 allows the electrode contact points 60 to be stimulated independently and/or unilaterally, as the response to stimulus may be localized and thus varied from one side of the midline to the other side.

Figure 5I:
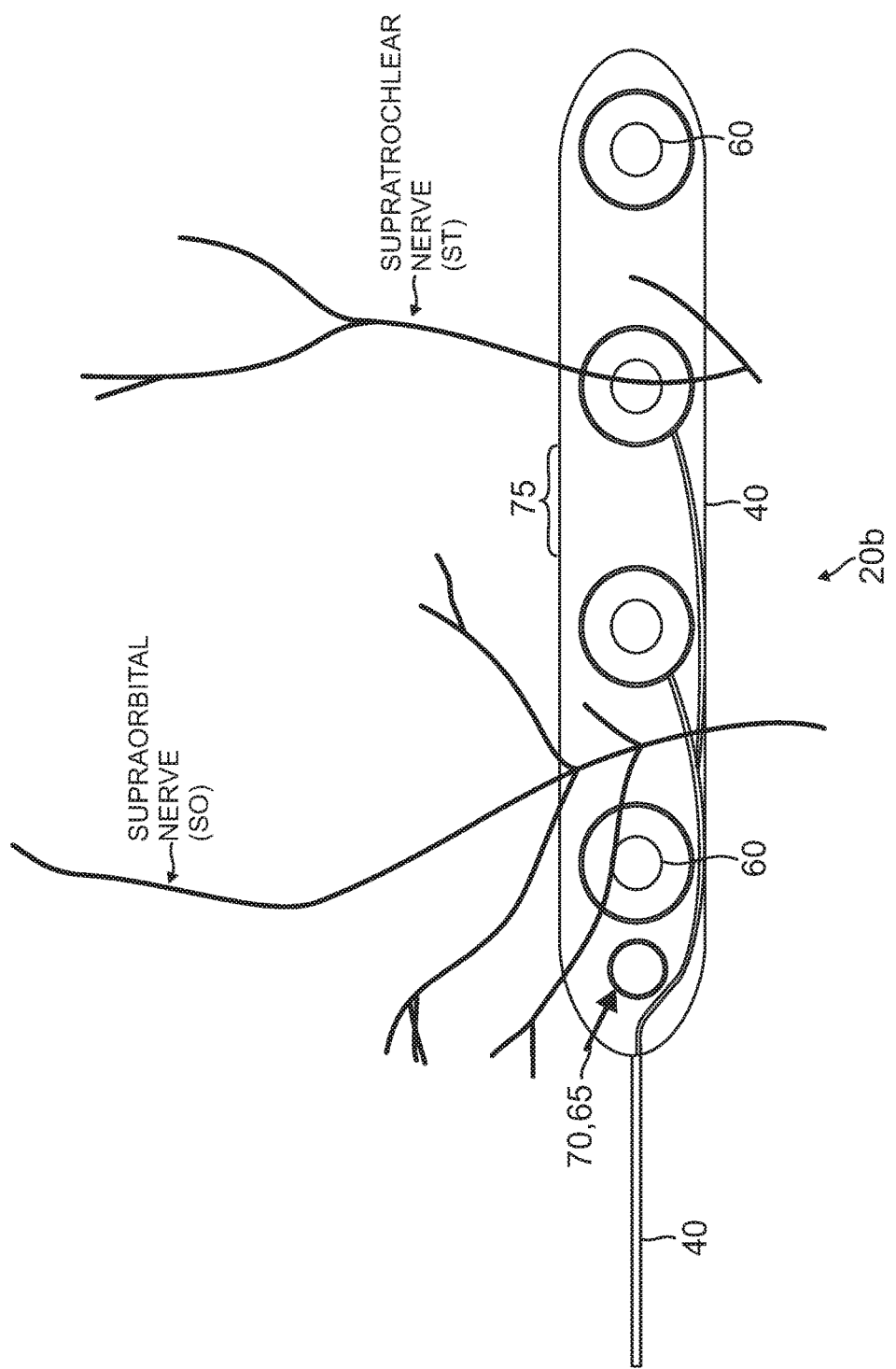
Figure 5J:
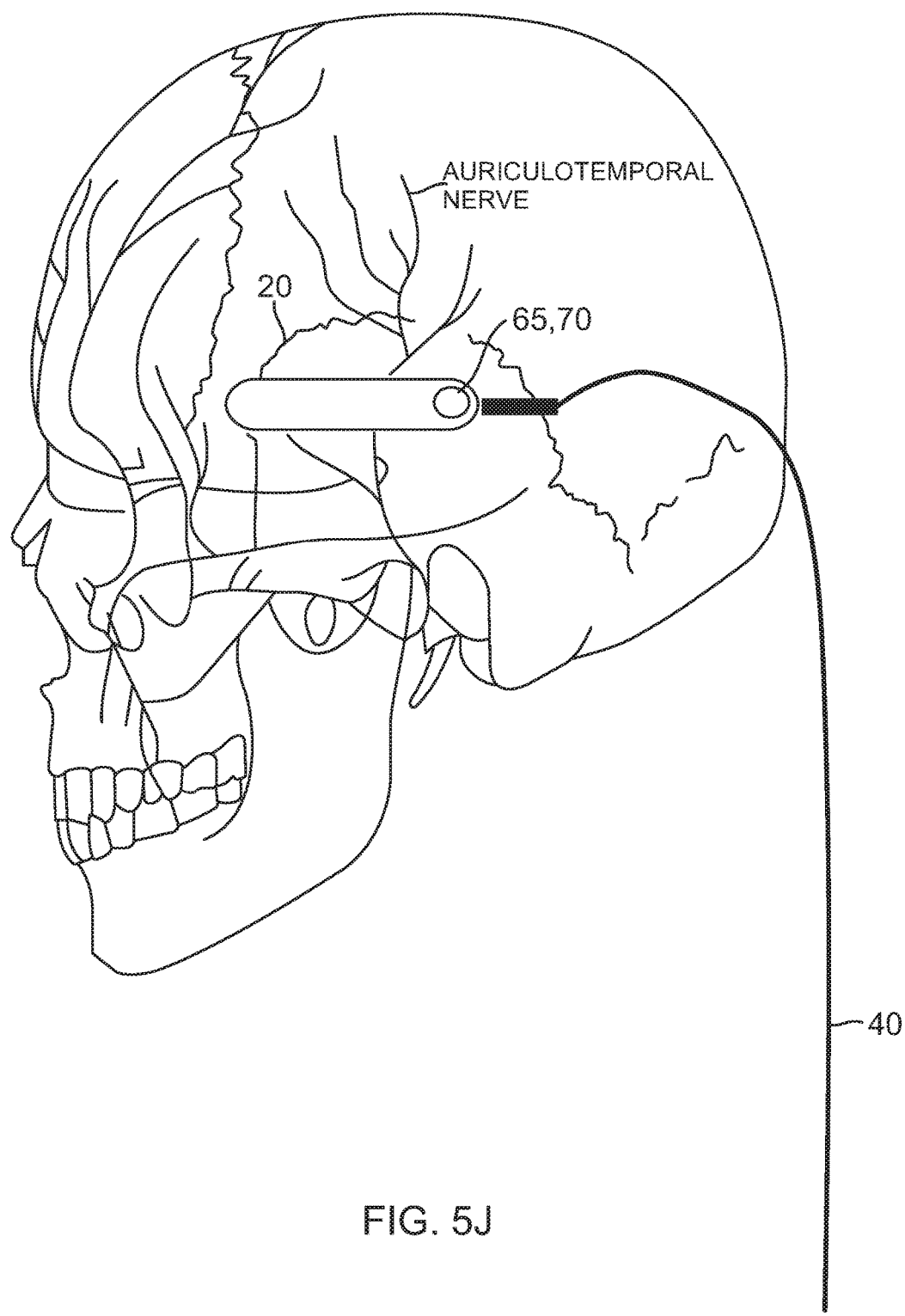
FIG. 5J illustrates an embodiment of an electrode assembly that may be used with the system of FIG. 2, wherein the assembly is configured for placement relative to the temporal lobe and auriculotemporal nerve.

In other embodiments, current may be stimulated in an orthogonal or perpendicular fashion to the nerve fiber. For example, as seen in FIG. 5I, a contact 60 that is lateral to the supraorbital nerve may form one anode/cathode terminal— the use of biphasic pulses makes a contact act as a cathode during one half cycle of the pulse and as an anode during the remaining half cycle of the pulse. A contact 60 that is medial to the supratrochlear forms the remaining anode/cathode terminal. In this fashion, current will be excited first in the lateral direction across each nerve fiber and then in the medial direction across each nerve fiber. Referring again to a "fiber-directed" embodiment such as shown in FIG. 5A, the current will instead be excited first in an afferent direction and then in the efferent direction for each biphasic pulse. Biphasic pulses have the advantage of no charge build up. Conversely, single phase pulses would involve the use of a dedicated cathode contact and a dedicated anode contact. Although such embodiments are within the scope of the disclosure, there is the danger of charge build up when a contact acts as a dedicated anode or cathode. Thus, such embodiments would be useful primarily for acute applications. But for chronic or prolonged treatments, the use of biphasic pulses eliminates the danger of charge buildup.

To excite a nerve fiber using orthogonally-directed current, one contact 60 should either overlay the nerve fiber or be to one side of the nerve fiber. The remaining contact can then be located to the opposing side of the nerve fiber. Such an arrangement is shown in FIG. 5I. But one can appreciate that a pair of contacts is involved in either a fiber-directed or orthogonally-directed embodiment. In a fiber-directed embodiment, both contacts overlay the nerve fiber. One contact is distally located on the fiber whereas the other is proximally located. For example, as shown in FIG. 5A for electrode 20*b*, one contact 60 is distally positioned away from the foramen whereas another contact 60 is proximally positioned towards the foramen. But in FIG. 5I, one contact 60 is positioned relatively lateral to the nerve fibers whereas another is positioned relatively medial to the nerve fibers. Should these medial and lateral contacts 60 form the anode/cathode terminals, current will thus alternate in the medial and lateral directions across the nerve. In that regard, it is well known that it is the cathode terminal that excites (depolarizes) a nerve fiber. In contrast, an anode terminal will tend to hyperpolarize the nerve fiber. For this reason, the anode terminal is commonly denoted as the reference of "indifferent" terminal. So if the pulses are not biphasic, a cathode terminal may be positioned to overlay or be adjacent (overlay but be slightly medial or lateral) to a given nerve fiber. The anode terminal location is not so critical.

But in a biphasic pulse embodiment, a given contact 60 acts as both a cathode and an anode. In its simplest embodiment, a pair of contacts 60 form cathode/anode terminals. While one contact acts as the anode, the other acts as the cathode, and vice versa. One can appreciate that such contacts may form groups. In other words, one lead 40 couples to a group of contacts 60 whereas another lead 40 couples to another group of contacts 60. While the one group acts as a cathode, the other group acts as an anode, and vice versa. Regardless of whether the contacts 60 are excited in such groups or just as pairs, one can appreciate that in a biphasic embodiment, the location of each contact 60 should be positioned appropriately in that each contact will be acting as a cathode during half of each biphasic pulse from pulse generator 30.

In a fiber-directed embodiment, one would thus want the contacts 60 located with regard to the nerve fiber such that current is first directed in the afferent direction (towards the ganglion) along the fiber and then in the efferent direction (away from the ganglion). Referring again to FIG. 2, each electrode 20*a* and 20*b* may be considered to have a proximal side (the side facing towards the supraorbital arch) and a distal side (the side facing towards the hairline). In such a fiber-directed embodiment, one contact 60 is thus located towards the distal side of the electrode body whereas an opposing contact 60 is located towards the proximal side of the electrode. In contrast, in an orthogonally-directed embodiment, the contacts 60 are located with regard to the nerve fiber such that current is directed across the nerve fiber in a lateral direction and then in a medial direction. Referring again to FIG. 5I, at least one contact 60 is thus located towards the medial end of the electrode body whereas an at least one opposing contact 60 is located towards the lateral end of the electrode body. One can appreciate that such embodiments may be combined such that a "diagonal" current could be excited that would have both fiber-directed and orthogonally-directed components.

While FIG. 2 illustrates an electrode assembly 20 implanted bilaterally and in other embodiments, the electrode assembly may be implanted unilaterally. While FIG. 2 illustrates an approach to implantation to stimulate the supraorbital and supratrochlear nerves, a similar process can be used in other subcutaneous locations to stimulate any of the major or minor branches of the trigeminal system.

Figure 6A:
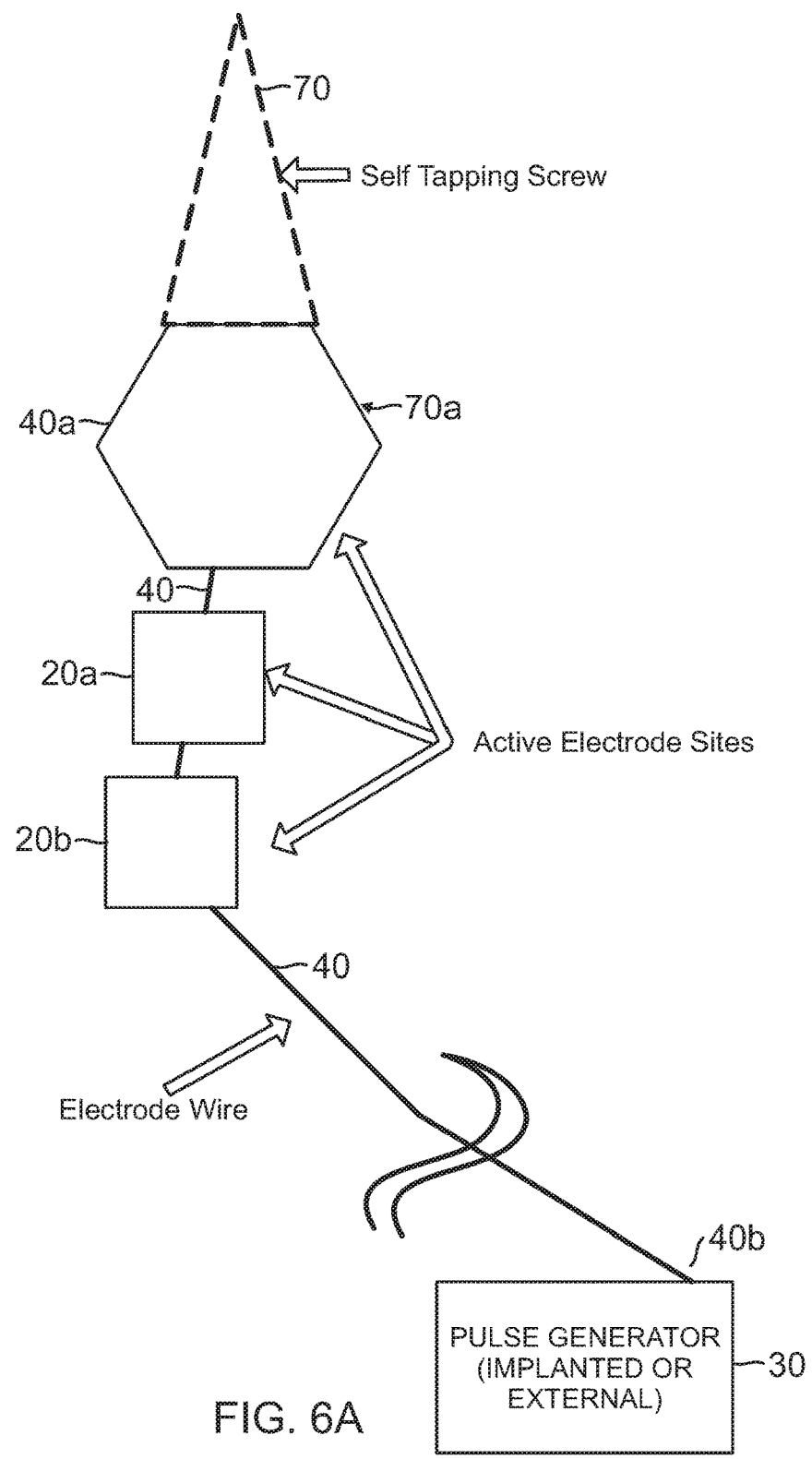
FIG. 6A illustrates another embodiment of an implantable electrode system according to aspects of the present disclosure.

In some embodiments, an implantable electrode system may be used for spinal nerve stimulation by stimulating a nerve as it exits from the vertebral foramina. In one embodiment, and as illustrated in FIG. 6A, and with reference to FIGS. 6B-6C, the anchoring device 70 may be a self-tapping screw, and is coupled to a distal end 40*a* of an insulated wire 40. The proximal end 40*b* of the wire is coupled to the pulse generator 30. The self-tapping screw 70 includes a hexagonal, electrically active head 70*a*. At least two electrodes 20*a* and 20*b* are also electrically coupled to the wire 40. In various embodiments, the electrodes 20*a* and 20*b* may be spaced between approximately 2 mm to 5 mm apart. Upon delivery, and as discussed in more detail with respect to FIGS. 6B-6C, the anchoring device 70 is secured to the border of a natural bony orifice, for example the foramen ovale, rotundum, maxillary, orbitalis, mandibular, lacerum, spinal foramina, etc. The device 70 anchors the electrode(s) such that the electrodes are near or in contact with the nerve, while permitting movement of the skeleton without interfering with the stimulation. Advantageously, the electrically active screw head 40*a* will stimulate the nerve bundle as it exits the vertebral foramina as the trajectory of the nerve exiting the foramina may not follow the wire attached to the screw head.

Figure 6C:
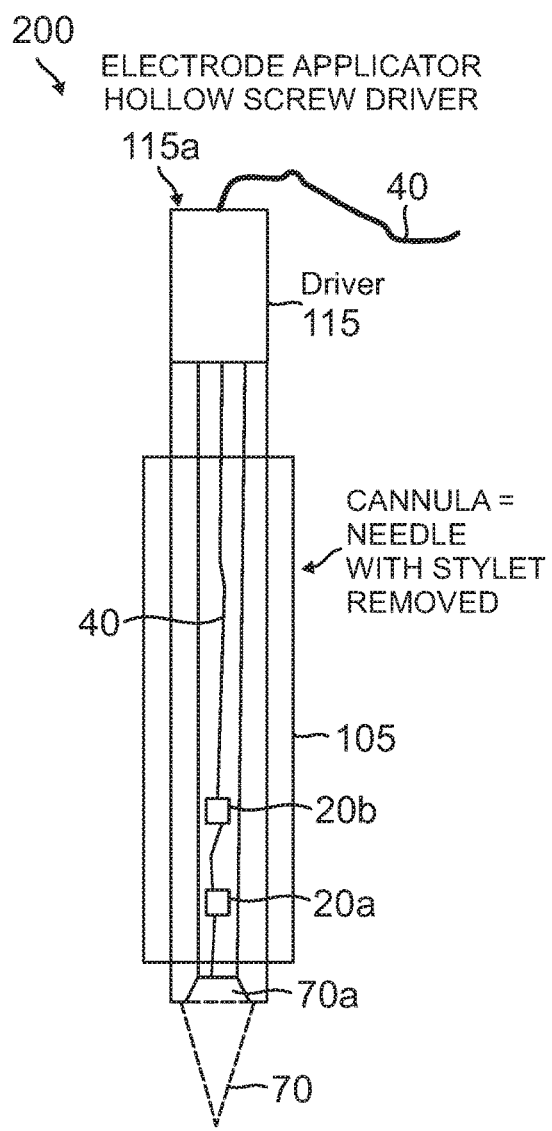
FIGS. 6B and 6C illustrate a minimally invasive delivery device that may be used to deliver an implantable electrode system as disclosed herein to a target bony region.
Figure 6B:
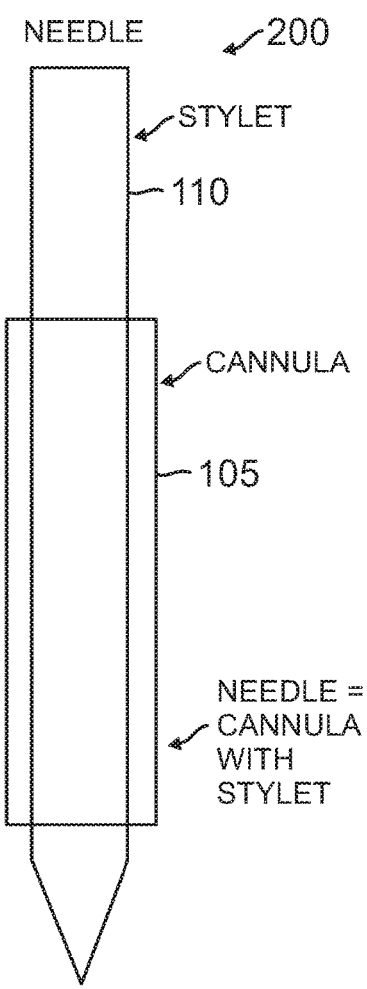

As shown in FIGS. 6B-6C, the electrode assembly 20, anchoring device 70 and lead wire 40 may be delivered via a delivery device 200. The delivery device 200 includes a cannula 105 and a stylet 110. The delivery device 200 may further include an applicator or driver 115, such as a hollow screw driver or wrench, to aid in implanting the anchoring device 70. The stylet is removably received in the cannula, and upon delivery of the cannula to the target location, the stylet is removed and the hollow screw driver 115 (wrench) is introduced to deliver the self-tapping screw 70 directed by the cannula. The length of the device 200 (applicator, cannula and stylet) will depend on the nerve to be stimulated and the distance between the skin and the target site into which the anchoring device will be delivered. For example, the trigeminal nerve is generally close to the skin and runs parallel to the skull surface with the supra-orbital foramen accessible and identifiable under fluoroscopy, the device 200 can be approximately 5-7 cm in length (including the handle of the driver).

To use, and as can be understood with reference to FIGS. 6B-6C, in one embodiment, a surgeon identifies the target location via intra-operative fluoroscopy, makes a stab-wound incision and percutaneously introduces the device 200 with the stylet 110. The device 200 is advanced to the target location under fluoroscopy guidance, and the stylet is removed from the cannula when the cannula is in direct contact with the target bone location. The anchoring device 70, electrode assembly 20 and lead wire 40 are held by the hollow screw driver 115 with the proximal end 40*b* of the wire exiting through the proximal end 115*a* of the screw driver 115. The screw driver 115 advances the assembly and anchoring device through the cannula and aids in securing the anchoring device 70 to the bone at the target location.

The other contacts 20a and 20b will stay in the soft tissue near the location of the nerve or its branches and will move with the soft tissue as the patient moves. Once the device 70 is in place, the screw driver is removed and the lead wire is tunneled to the location of the pulse generator. In one embodiment, the anchoring device forms a single anode/cathode contact. The stimulation of a nerve of course requires another anode/cathode contact. Thus, a second anchoring device and corresponding lead may be percutaneously implanted adjacent the first anchoring device.

Following placement of the electrode assembly, it is then connected to an implanted neurostimulator 30 via the implanted electrical cables 40, which are placed under the patient's skin. In the embodiment of the system shown in FIG. 2, the stimulation via the neurostimulator 30 is via electrical cables 40. In alternative embodiments, the electrical stimulation can be performed wirelessly, with an external, non-implanted neurostimulator, which uses inductive coupling to deliver energy to the implanted electrode assembly 20. In still other embodiments, the electrode assembly 20 is implanted, while the neurostimulator is placed external to the body, and the two are connected via electrical cable(s) 40.

Stimulation may be provided by selecting operational parameters such as the pulse duration, the electrode current, the duty cycle and the stimulation frequency; the parameters are selected to ensure that the total charge, the charge density, and charge per phase are well within accepted safety limits for the scalp or facial tissue, other tissues surrounding nerves and brain. The values of the operational parameters are advantageously selected such that a patient will experience a stimulation sensation, such as mild tingling over the forehead and scalp, without causing the patient significant discomfort or pain and with minimal current penetration to the brain. These values may vary according to the treatment of interest, however the parameters are at a charge density significantly less than 10 $\mu C/cm^2$ at a current density below 25 $mA/cm^2$. In one embodiment, the output current is 3 mA at 250 μsec, with an electrode radius of 0.2 cm and, therefore, the charge density is 0.59 $\mu C/cm^2$.

Additionally, in some embodiments, selection of the electrical stimulation parameters, electrode design, and inter-electrode distance is made such that the electrical stimulation zone includes the superficial elements of the trigeminal nerves (approximately 3-4 mm deep), while preventing or minimizing current penetration beneath the bone tissue of the skull. In some embodiments, lower currents (e.g. 0.05-5 mA) and careful electrode placement may be selected to avoid recruitment of nerves supplying pain sensation to the teeth. In some embodiments, lower currents (e.g. 0.05-5 mA) may also be selected to avoid penetration of the current into the skull and brain, especially in supraorbital locations.

In various embodiments, the stimulation parameters delivered by the implanted pulse generator (neurostimulator) may be determined (programmed) at the time the device is surgically implanted. In other embodiments, these parameters may be modified, controlled, or otherwise programmed by an external device. This external programming element communicates with the implanted components wirelessly. This may take place, for example, by radiofrequency signals, by inductive coupling, or other means apparent to one skilled in the art.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An implantable electrode assembly for stimulation of the ophthalmic nerves, comprising
    a pulse generator;
    an electrode body having a first end, an opposing second end, a stimulating surface, and a sensing surface opposing the stimulating surface;
    a pair of electrical contacts disposed on or integrally formed on the stimulating surface of the electrode body such that one of the electrical contacts in the pair is located near the first end and a remaining one of the electrical contacts in the pair is located near the second end, the pair of electrical contacts being electrically coupled to the pulse generator and spaced apart such that the pair of electrical contacts are configured to excite an orthogonally-directed current across a supraorbital nerve and across an adjacent supratrochlear nerve;
    one or more sensing contacts disposed on or integrally formed on the sensing surface of the electrode body and electrically coupled to the pulse generator and configured to detect brain electrical activities;
    an insulating region defined between the electrical contacts;
    an aperture defined in the electrode body, wherein the aperture is configured to receive an anchoring device.

2. The implantable electrode assembly of claim 1, wherein the aperture is located adjacent a proximal end of the electrode body.

3. The implantable electrode assembly of claim 1, wherein the aperture is located adjacent a distal end of the electrode body.

4. The implantable electrode assembly of claim 1, wherein the aperture is located centrally in the electrode body.

* * * * *